United States Patent [19]

Heinz et al.

[11] Patent Number: 5,814,646

[45] Date of Patent: Sep. 29, 1998

[54] INHIBITORS OF AMYLOID BETA-PROTEIN PRODUCTION

[75] Inventors: Lawrence J. Heinz, Pittsboro; Jill A. Panetta, Zionsville; Michael L. Phillips, Indianapolis; Jon K. Reel, Carmel; John K. Shadle, Fishers; Richard L. Simon; Celia A. Whitesitt, both of Greenwood, all of Ind.

[73] Assignee: Eli Lilly and Company, Indianapolis, Ind.

[21] Appl. No.: 398,188

[22] Filed: Mar. 2, 1995

[51] Int. Cl.$^6$ .............. A61K 31/415; A61K 31/425; C07D 285/135
[52] U.S. Cl. ............................ 514/363; 548/140
[58] Field of Search ................. 548/140; 514/363

[56] References Cited

U.S. PATENT DOCUMENTS

| | | | |
|---|---|---|---|
| 3,990,879 | 11/1976 | Soper | 548/140 |
| 4,021,225 | 5/1977 | Hedrich | 548/140 |
| 4,174,398 | 11/1979 | Regel | 548/140 |
| 4,175,081 | 11/1979 | Driscoll | 548/140 |
| 4,518,414 | 5/1985 | Schirmer | 544/63 |
| 4,576,629 | 3/1986 | Morland | 548/140 |
| 4,599,424 | 7/1986 | Driscoll | 548/140 |
| 4,639,526 | 1/1987 | Metzger | 548/140 |
| 4,686,294 | 8/1987 | Hoegerle | 548/140 |
| 4,835,168 | 5/1989 | Paget | 548/140 |
| 4,876,044 | 10/1989 | Cebalo | 548/140 |
| 4,987,233 | 1/1991 | Achgill | 548/140 |
| 5,087,284 | 2/1992 | Driscoll | 546/209 |

OTHER PUBLICATIONS

U.S. application No. 08/397466 Reel et al. Mar. 02, 1995.
LeBlanc, Metabolic Brain Disease, vol 9(1), pp 3–31, 1994.
Yankner, Science, vol 250, pp279–281, 12 Oct. 1990.
Selkoe, Neuron, vol 6, pp 487–498, Apr. 1991.
Schenk, Journal of Medicinal Chemistry, vol 38(21), pp414–4154, 13 Oct. 1995.

*Primary Examiner*—Alan L. Rotman
*Assistant Examiner*—D. Margaret M. Mach
*Attorney, Agent, or Firm*—Arleen Palmberg; David E. Boone

[57] ABSTRACT

A method of protecting a warm-blooded mammal from the progression of Alzheimer's disease, which comprises administering an effective amount of a compound of general formula.

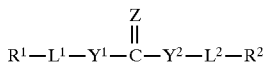

in which:

$R^1$ represents an optionally substituted aromatic or heteroaromatic group;

$L^1$ and $L^2$ each independently represents a bond or an unbranched (1–4C) alkylene group, which alkylene group may optionally bear a (1–4C) alkyl, phenyl or phenyl (1–2C) alkyl substituent;

one of $Y^1$ and $Y^2$ represents $NR^3$ and the other represents O, S or $NR^3$, in which $R^3$ represent hydrogen, hydroxyl, (1–4C) alkoxy, (1–4C) alkyl or di (1–4C) alkylamino;

Z represents O or S; and $R^2$ represents (3–8C) cycloalkyl, heterocyclyl, and optionally substituted aromatic or heteroaromatic group, or together with $L^2$, (1–10C) alkyl;

or a pharmaceutically acceptable salt thereof.

6 Claims, No Drawings

INHIBITORS OF AMYLOID BETA-PROTEIN PRODUCTION

The present invention relates to the use of certain urea derivatives as inhibitors of amyloid beta-protein production. It also relates to novel urea derivatives, to processes for their preparation and to pharmaceutical compositions containing them.

Amyloid beta-protein (Aβ) is a neurotoxic polypeptide containing about 40 amino acid residues. It is produced by enzymatic cleavage of a larger precursor protein, beta-amyloid precursor protein, which is encoded by a gene on human chromosome 21, and is found in the brains of individuals suffering from Alzheimer's disease in deposits known as senile plaques. It is now widely believed that Aβ is involved in the pathogenesis of Alzheimer's disease, and substantial efforts are being made to find ways of intervening in this involvement, for example by inhibiting the production of Aβ.

It has now been found that certain urea derivatives, some of which are novel, are capable of inhibiting the production of Aβ in cells.

The present invention provides a method of inhibiting the production of Aβ peptide in a biological system, which comprises administering an effective amount of a compound of general formula.

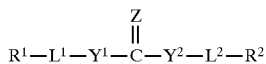

in which:

$R^1$ represents an optionally substituted aromatic or heteroaromatic group;

$L^1$ and $L^2$ each independently represents a bond or an unbranched (1–4C) alkylene group, which alkylene group may optionally bear a (1–4C) alkyl, phenyl or phenyl (1–2C) alkyl substituent;

one of $Y^1$ and $Y^2$ represents $NR^3$ and the other represents O, S or $NR^3$, in which $R^3$ represent hydrogen, hydroxyl, (1–4C) alkoxy, (1–4C) alkyl or di (1–4C) alkylamino;

Z represents O or S; and $R^2$ represents (3–8C) cycloalkyl, heterocyclyl, an optionally substituted aromatic or heteroaromatic group, or together with $L^2$, (1–10C) alkyl;

or a pharmaceutically acceptable salt thereof.

It has been found that urea derivatives of formula I are capable of inhibiting the production of Aβ in whole cells. Accordingly, it is believed that these compounds will be capable of inhibiting the production of Aβ generally in biological systems, and will be capable of inhibiting the accumulation of Aβ in senile plaques in a warm blooded mammal, such as man. The urea derivatives should therefore be capable of protecting a warm blooded mammal, such as man, from the progression of Alzheimer's disease.

According to another aspect, therefore, the present invention provides a method of inhibiting the accumulation of Aβ in senile plaques in a warm blooded mammal, which comprises administering an effective amount of a compound of formula I, or a pharmaceutically acceptable salt thereof.

According to yet another aspect, the present invention provides a method of protecting a warm blooded mammal from the progression of Alzheimer's disease, which comprises administering an effective amount of a compound of formula I, or a pharmaceutically acceptable salt thereof.

The present invention also provides the use of a compound of formula I, or a pharmaceutically acceptable salt thereof, in the manufacture of a medicament for the treatment of Alzheimer's disease.

The urea derivatives which have been found to be capable of inhibiting the production of Aβ in whole cells possess a diverse range of structures. Accordingly it is believed that they are representatives of a new, broad structural class of inhibitor of Aβ production, as defined herein with reference to formula I.

As used herein with reference to formula I, the term aromatic group includes phenyl and naphthyl.

The term heteroaromatic group includes a 5–6 membered ring containing a heteroatom selected from oxygen, sulfur and nitrogen and up to three additional nitrogen atoms, the remaining ring atoms all being carbon atoms, said ring, optionally being fused to a benzene ring. Examples of heteroaromatic groups include furyl, thienyl, oxazolyl, isoxazolyl, thiazolyl, isothiazolyl, oxadiazolyl, thiadiazolyl, imidazolyl, pyridyl, pyrimidyl, triazinyl, benzofuryl, benzothienyl, benzothiazolyl, benzimidazolyl, indolyl and quinolyl.

The term optionally substituted, as used in optionally substituted aromatic or heteroaromatic group means that the group is unsubstituted or substituted by one or more, for example 1, 2 or 3, substituents which do not interfere with the ability of the compound of formula I to inhibit Aβ production.

Examples of substituents which may be present in an optionally substituted aromatic or heteroaromatic group (for example an optionally substituted phenyl group) include hydroxy, halogeno, (1–8C) alkyl, methylenedioxy, carboxy, (1–8C) alkoxycarbonyl, halo(1–8C) alkyl and groups of formula $XR^4$, in which $R^4$ represents (1–6C) alkyl, phenyl which is unsubstituted or substituted by 1,2 or 3 of (1–6C) alkyl, (1–6C) alkoxy, amino, halogeno, (1–6C) alkanoyl, benzoyl, phenyl, hydroxy and halo (1–6C) alkyl, naphthyl, furyl, thienyl, pyridyl, benzothienyl, quinolyl, indolyl and benzimidazolyl, and X represents O, $CH_2$, $OCH_2$, S, SO, $SO_2$, NH, CO or CONH.

The term (1–8C) alkyl includes (1–6C) alkyl and (1–4C) alkyl. Examples of (1–8C) alkyl groups are methyl, ethyl, propyl, isopropyl, butyl, isobutyl, tert-butyl, pentyl and hexyl.

The term (1–8C) alkoxy includes (1–6C) alkoxy and (1–4C) alkoxy. Examples of a (1–8C) alkoxy group are methoxy, ethoxy and butoxy.

Examples of a halogen atom are fluoro, chloro and bromo.

Halo(1–8C) alkyl includes halo (1–6C) alkyl, for example trifluoromethyl.

An example of a (1–8C) alkoxycarbonyl group is methoxycarbonyl.

An example of a (1–6C) alkanoyl group is acetyl.

Examples of a (1–4C) alkylene group are methylene and ethylene.

An example of a phenyl(1–2C)alkyl group is benzyl.

An example of a di (1–4C) alkylamino group is dimethylamino.

Examples of a (3–8C) cycloalkyl group are cyclopropyl, cyclobutyl, cyclopentyl and cyclohexyl.

The term heterocyclyl, as used herein includes a non-aromatic 4–6 membered ring containing one or two heteroatoms selected independently from oxygen, sulfur and nitrogen, the remaining ring atoms all being carbon atoms. An example of heterocyclyl is piperidinyl.

Preferably $R^2$ represents cyclopentyl; cyclohexyl; piperdinyl; phenyl which is unsubstituted or substituted by methylenedioxy or by one or two substituents independently selected from halogeno, (1–4C) alkyl, (1–4C) alkoxy, fluoro (1–4C) alkyl and fluoro (1–4C) alkoxy; naphthyl; pyridyl or, together with $L^2$, represents 5–10C) alkyl.

More preferably $R^2$ represents a phenyl group which is unsubstituted or substituted by one or two substituents selected from fluoro, chloro, methyl, methoxy and trifluoromethyl.

Examples of specific values for $R^2$ are 2,3-dichlorophenyl, 4,5-dichloro-2-methylphenyl, 4-methylthiophenyl, 2-trifluoromethylphenyl, 3-trifluoromethylphenyl, 4-t-butylphenyl, 2,6-dimethylphenyl, 3-methylthiophenyl, phenyl, 2-methylphenyl, 3-methylphenyl, 4-methylphenyl, 4-fluoromethyl, 4-chlorophenyl, 3,4-dichlorophenyl, 3-chloro-4-methylphenyl, 3,4-dimethylphenyl, 3,4-dimethoxyphenyl, 3,4-methylenedioxyphenyl, 3-chlorophenyl, 2,4-dichlorophenyl, 3-fluorophenyl, 3-methoxyphenyl, 2-chloro-3-trifluoro-methylphenyl, 4-chloro-3-trifluoromethylphenyl, 4-(n-butoxy)phenyl, 2-chlorophenyl, 3-bromophenyl, 4-bromophenyl, 2-methoxyphenyl, 4-methoxyphenyl, 2,4-difluorophenyl, 3,4-difluorophenyl, 2-chloro-4-fluorophenyl, 3-chloro-4-fluorophenyl, 4-fluoro-2-trifluoromethylphenyl, 3,4,5-trichlorophenyl, 1-naphthyl, 2-pyridyl, 3-pyridyl, 4-pyridyl, N-t-butoxycarbonyl-2-piperidinyl, N-t-butoxycarbonyl-3-piperidinyl, 2-piperidinyl, 3-piperidinyl and 2-trifluoromethyl-1,3,4-thiadiazoyl, or together with $L^2$, methyl or hexyl.

Most preferably $R^2$ represents 3,4-dichlorophenyl or 4-chloro-3-trifluoromethylphenyl.

$R^1$ preferably represents a phenyl, naphthyl, furyl, thienyl, oxazolyl, isoxazolyl, thiazolyl, isothiazolyl, oxadiazolyl, thiadiazolyl, imidazolyl, pyridyl, pyrimidyl, triazinyl, benzofuryl, benzothienyl, benzothiazolyl or benzimidazolyl group, which group is unsubstituted or substituted by one or two substituents independently selected from hydroxy, halogeno, (1–6C) alkyl, carboxy, (1–4C) alkoxycarbonyl, halo (1–6C) alkyl and groups of formula $XR^4$ in which $R^4$ represents (1–6C)alkyl, phenyl which is unsubstituted or substituted by one, two or three of (1–6C) alkyl, (1–6C) alkoxy, amino, halogeno, (1–6C) alkanoyl, benzoyl, phenyl, hydroxy and halo (1–6C) alkyl, naphthyl, furyl, thienyl, pyridyl, benzothienyl, quinolyl, indolyl and benzimidazolyl and X represents O, $CH_2$, $OCH_2$, S, SO, $SO_2$, NH, CO or CONH.

More preferably $R^1$ represents a 3-phenyl, 4-phenyl or 1,3,4-thiadiazol-2-yl group which is unsubstituted or substituted as defined hereinabove.

For example $R^1$ may represent a group of formula IIa or IIb

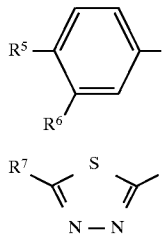

Iia

IIb in which one of $R^5$ and $R^6$ represents hydrogen and the other represents a group of formula $XR^4$, and $R^7$ represents hydrogen, (1–8C) alkyl, halo (1–8C) alkyl, (1–8C) alkylthio, (1–8C) alkoxy or halogeno.

Examples of specific values for $R^1$ are selected from 4-(4-(t-butyl)phenoxy)phenyl, 4-(2-quinolinylthio)phenyl, 3-phenoxyphenyl, 4-phenoxyphenyl, 3-(4-t-butylphenoxy) phenyl, 3-(4-n-butylphenoxy)phenyl, 4-(3-t-butylphenoxy) phenyl, 2-(4-t-butylphenoxy)phenyl, 3-(3-t-butylphenoxy) phenyl, 4-(2-t-butylphenoxy)phenyl, 3-(4-t-butylbenzyloxy)phenyl, 4-(4-t-butylbenzyloxy)phenyl, 4-(2-phenylbenzyloxy)phenyl), 4-(3,4-dichlorobenzyloxy) phenyl, 4-(3,4-difluorobenzyloxy)phenyl, 4-(2,5-dimethylbenzyloxy)-phenyl, 4-(3,5-dimethoxybenzyloxy) phenyl, 4-(4-n-butylbenzyloxy)phenyl, 4-(2,6-dichlorobenzyloxy)-phenyl, 3-(4-butoxybenzyloxyphenyl, 4-(4-acetyl-3-hydroxy-2-propylbenzyloxy)phenyl, 4-(4-benzoyl-3-hydroxy-2-propylbenzyloxy)phenyl, 2-propylbenzyloxy)phenyl, 3-(3,5-di-t-butyl-4-methoxybenzyloxy)phenyl, 4-(3,5-di-t-butyl-4-methoxybenzyloxy)phenyl, 2-(2-phenylbenzyloxy)phenyl, 4-(2-phenylbenzyloxy)phenyl, 4-biphenyl, 4-(4-t-butylphenyl)-phenyl, 3-(4-t-butylbenzamido)phenyl, 3-(4-t-butylphenylthio)phenyl, 4-(4-t-butylphenylthio)phenyl, 3-(4-t-butylphenylsulfinyl)phenyl, 3-(4-t-butylphenylsulfonyl)-phenyl, 4-(4-t-butylphenylthiomethyl) phenyl, 4-(4-1,1-dimethylpropylphenoxymethyl)phenyl, 3-(2-propyl-4-t-butylphenoxyphenyl, 5-quinolinyl, 2-benzothiazolyl, 2-pyrimidinyl, 4-chlorophenyl, 2-benzimidazolyl, 2-dimethylaminopropylthiophenyl, 2-methoxycarbonylphenyl, 2-(5,6-dimethyl) benzimidazolyl, 2,4-dimethoxyphenyl, 4-(3,4-dichlorophenylthio)phenyl, 3-trifluoromethylphenyl, 4-methylthiophenyl, 3-bromo-4-methylthiophenyl, 2-chlorophenyl, phenyl, 3,4-dichlorophenyl, 4-methylsulfonylphenyl, 3-bromo-4-methylphenyl, 2,5-dichloro-4-methylthiophenyl, 3-bromo-4-methylthiophenyl, 3-methoxy-4-methoxycarbonylphenyl, 4-chloro-3-trifluoromethylphenyl, 4-(4-t-butyl-2-propylphenoxy) phenyl, 4-acetyl-3-hydroxy-2-propylphenyl, 3,4-dichlorophenyl, 4-(4-(ethoxycarbonyl-2-quinolylthio) phenyl, 4-(6-chloro-2-quinolylthio)phenyl, 4-(4-phenyl-2-quinolylthio)phenyl, 4-(4-quinolylthio)phenyl, 4-(7-trifluoromethyl-4-quinolylthio)phenyl, 4-(2-naphthylthio) phenyl, 4-(1-naphthylthio)phenyl, 4-(2-benzimidazolylthio) phenyl, 4-(2-benzoxazolylthio)phenyl, 4-(2-benzothiazolylthio)phenyl, 4-(5-chloro-2-benzothiazolylthio)phenyl, 4-(2-quinolylsulfonyl)phenyl, 4-(2-quinolylsulfonyl)phenyl, 4-(2-quinolylamino)phenyl, 4-(2-quinolyloxy)phenyl, 4-(2-quinolylthio)phenyl, 4-(6-phenyl-3-pyridazylthio)phenyl, 4-(2-pyridylthio)phenyl, 4-(5-nitroquinolylthio)phenyl, 4-(4-isopropylsulfonyl) phenyl, 2-pyridyl, 6-1,2,5-triazinyl, 1-piperidinyl, 1-ethyl-3-piperdinyl, 2,2,6,6-tetramethyl-4-piperidinyl, 5-chloro-1,3,4-thiadiazol-2-yl, 2-methoxycarbonylbenzothiophen-3-yl, 5-methyl-1,3,4-thiadiazol-2-yl, 1,3,4-thiadiazol-2-yl, 5-trifluoromethyl-1,3,4-thiadiazol-2-yl, 5-t-butyl-1,3,4-thiadiazol-2-yl, 5-(2-chloro-1,1-dimethylethyl)-1,3,4-thiadiazol-2-yl, 5-hexylthio-1,3,4-thiadiazol-2-yl, 5-bromo-1,3,4-thiadiazol-2-yl, 2-oxazolyl, 5-methylisoxazol-3-yl, 2-thiazolyl, 4,5-dihydrothiazolyl, 3-t-butylisoxazol-5yl, and 3-t-butyl-1,2,4-oxadiazol-5-yl.

Preferably one of $Y^1$ and $Y^2$ represents NH and the other represents S, NH or NOH.

One of $L^1$ and $L^2$ preferably represents a bond and the other preferably represents a bond or methylene, ethylidene, propylidene, heptylidine or benzylidine. More preferably $L^1$ and $L^2$ each represents a bond.

A preferred group of compounds of formula I are those of the formula Ia

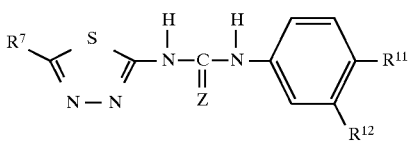

in which

Z is O or S;

$R^{11}$ is a halogen atom;

$R^{12}$ is a halogen atom or a trifluoromethyl group; and $R^7$ is hydrogen, (1–8C)alkyl, (1–8C)haloalkyl, (1–8C) alkylthio, (1–8C)alkoxy or halogen;

or a pharmaceutically acceptable salt thereof.

In this group of compounds Z is preferably O, $R^{11}$ is preferably a fluorine or chlorine atom, and $R^{12}$ is preferably a chlorine atom or a trifluoromethyl group. Examples of values for $R^7$ are hydrogen, methyl, t-butyl, trifluoromethyl, 2-chloro-2-methylpropyl, hexylthio, bromo and chloro.

Another preferred group of compounds of formula I are those of the formula Ib

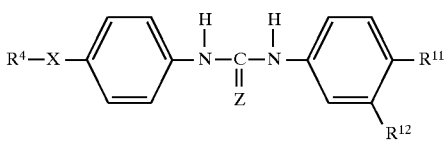

in which

Z is O or S;

$R^{11}$ is a halogen atom;

$R^{12}$ is a halogen atom or a trifluoromethyl group;

X is S, SO, $SO_2$, O or NH; and $R^4$ is naphthyl, quinolinyl, benzimidazolyl, pyridyl, pyridazinyl, benzoxazolyl or benzothiazolyl, unsubstituted or substituted by one or two substituents selected from a halogen atom, (1–4C)alkyl, (1–4C)alkoxy, nitro, (1–4C)alkoxycarbonyl, halo(1–4C)alkyl, and phenyl;

or a pharmaceutically acceptable salt thereof.

In this group of compounds, X is preferably S, Z is preferably S, $R^4$ is preferably unsubstituted or substituted naphth-1-yl, naphth-2-yl, quinolin-2-yl, quinolin-4-yl, quinolin-6-yl, benzimidazol-2-yl, benzoxazol-2-yl or benzothiazol-2-yl, and $R^{11}$ is preferably chlorine and $R^{12}$ is preferably chlorine or trifluoromethyl. Examples of particular values for $R^4$ are naphth-1-yl, naphth-2-yl, quinolin-2-yl, 6-chloroquinolin-2-yl, 6-methoxyquinolin-2-yl, 5-nitroquinolin-6-yl, 4-ethoxycarbonylquinolin-2-yl, 4-phenylquinolin-2-yl, 7-trifluoromethylquinolin-4-yl, quinolin-4-yl, benzimidazol-2-yl, benzoxazol-2-yl, benzothiazol-2-yl, 5-chloro-benzothiazol-2-yl, 6-phenylpyrazin-3-yl or pyridin-2-yl.

Particularly preferred compounds of formula I for use in the method according to the invention are 1-1,3,4-thiadiazol-2-yl-3-(3,4-dichlorophenyl)urea;

1-(5-chloro-1,3,4-thiadiazol-2-yl)-3-(3,4-dichlorophenyl) urea;

1-(5-trifluoromethyl-1,3,4-thiadiazol-2-yl)-3-(3,4-dichlorophenyl)urea;

1-(5-t-butyl-1,3,4-thiadiazol-2-yl)-3-(3,4-dichlorophenyl) urea;

1-[5-(2-chloro-1,1-dimethylethyl)-1,3,4-thiadiazol-2-yl]-3-(3,4-dichlorophenyl)urea;

1-(5-hexylthio-1,3,4-thiadiazol-2-yl)-3-(3,4-dichlorophenyl)urea;

1-(5-bromo-1,3,4-thiadiazol-2-yl)-3-(3,4-dichlorophenyl) urea;

1-(5-methyl-1,3,4-thiadiazol-2-yl)-3-(4-fluoro-3-chlorophenyl)urea; and 1-(5-methyl-1,3,4-thiadiazol-2-yl)-3-(3,4-dichlorophenyl) urea.

Some of the compounds of formula I, for example the compounds of formula Ib, are believed to be novel.

The present invention also provides the novel compounds of formula I, and their pharmaceutically acceptable salts, processes for their preparation and pharmaceutical compositions containing them.

The term "pharmaceutically acceptable salts" refers to salts of the compounds of the above formula which are substantially non-toxic to living organisms. Typical pharmaceutically acceptable salts include those salts prepared by reaction of the compounds of the above formula I with a pharmaceutically acceptable mineral or organic acid, or a pharmaceutically acceptable alkali metal or organic base, depending on the types of substituents present on the compounds of the formula.

Examples of pharmaceutically acceptable mineral acids which may be used to prepare pharmaceutically acceptable salts include hydrochloric acid, phosphoric acid, sulfuric acid, hydrobromic acid, hydriodic acid, phosphorous acid and the like. Examples of pharmaceutically acceptable organic acids which may be used to prepare pharmaceutically acceptable salts include aliphatic mono and dicarboxylic acids, oxalic acid, carbonic acid, citric acid, succinic acid, phenyl-substituted alkynic acids, aliphatic and aromatic sulfonic acids and the like. Such pharmaceutically acceptable salts prepared from mineral or organic acids thus include hydrochloride, hydrobromide, nitrate, sulfate, pyrosulfate, bisulfate, sulfite, bisulfite, phosphate, monohydrogenphosphate, dihydrogenphosphate, metaphosphate, pyrophosphate, hydroxide, hydrofluoride, acetate, propionate, formate, oxalate, citrate, lactate, p-toluenesulfonate, methanesulfonate, maleate, and the like.

The compounds of formula I may be prepared by methods well known in the art, many compounds of formula I being known. See for example, U.S. Pat. No. 3,990,879.

Thus, compounds of formula I in which Z is O or S may be prepared by reacting a compound of formula III $$R^1\text{—}L^1\text{—}A^1 \qquad \text{III}$$

with a compound of formula IV $$A^2\text{—}L^2\text{—}R^2 \qquad \text{IV}$$

in which one of $A^1$ and $A^2$ represents —$NH_2$ and the other represents —NCZ or —NHC(Z)$Z^a$ in which Z is O or S, and $Z^a$ is a leaving atom or group.

$Z^a$ may represent, for example, an amine group such as —$NH_2$, an alkythio group such as methylthio an aryloxy group such as phenoxy, or an acetylene group, such as a (2–10C) alk-1-ynyl group.

When the other of $A^1$ and $A^2$ represents —NCZ, the reaction is conveniently performed in the presence of solvent such as water, an ether, for example tetrahydrofuran, a halogenated hydrocarbon, such as dichloromethane, or an amide such as dimethylformamide. The temperature at which the reaction is conducted is conveniently in the range of from 0° to 150° C. Optionally the reaction may be performed in the presence of a base, for example a tertiary amine, such as dimethylaminopyridine, or an alkali metal carbonate such as potassium carbonate.

When the other of $A^1$ and $A^2$ represent —NHC(Z)$Z^a$ in which $Z^a$ represents an acetylene group, the reaction is preferably performed in the presence of an alkali metal amide, such as sodium amide. The reaction is conveniently performed at a temperature in the range of from 0° to 50° C.

When the other of $A^1$ and $A^2$ represents —NHC(Z)$Z^a$ in which $Z^a$ represents a leaving atom or group other than an acetylene group, the reaction is conveniently performed at a temperature in the range of from 0° to 150° C. Suitable solvents include acetic acid, esters, such as ethyl acetate and ethers such as tetahydrofuran.

The compounds of formula III and IV in which the other of $A^1$ and $A^2$ represents —NC or —NCH(Z)$Z^a$ may be prepared by methods known in the art from the corresponding compounds of formula III or IV respectively in which $A^1$ or $A^2$ respectively represents —$NH_2$. For example, a compound of formula III or IV in which $A^1$ or $A^2$ represents —$NH_2$ may be converted into the corresponding compound in which $A^1$ or $A^2$ represents —NCZ by reaction with phosgene, and into a corresponding compound in which $A^1$ or $A^2$ represents —$NHCONH_2$ by reaction with an alkali metal cyanate, such as sodium cyanate.

The ability of a compound to inhibit the production of Aβ in a biological system may be demonstrated by the following test method.

Two cell lines (human kidney cell line 293 and Chinese hamster ovary cell line CHO) were stably transfected with the gene for APP-751 containing the double mutation $Lys_{651}$-$Met_{652}$ to $Asn_{651}$-$Leu_{652}$ (APP-751 numbering) commonly called the Swedish mutation using the method described in Citron et al., (1992) Nature 360:672–674. The transfected cell lines were designated as 293 751 SWE and CHO 751 SWE, and were plated in Corning 96 well plates at $2.5 \times 10^4$ or $1 \times 10^4$ cells per well respectively in Dulbecco's minimal essential media plus 10% fetal bovine serum. Following overnight incubation at 37° C. in an incubator equilibrated with 10% carbon dioxide ($CO_2$), the media were removed and replaced with 200 μL per well of media containing a test compound. After a two hour pretreatment period, the media were again removed and replaced with fresh media containing the test compound and the cells were incubated for an additional two hours.

Test compound stocks were prepared in DMSO such that at the final concentration used in the treatment, the concentration of DMSO did no exceed 0.5%. After treatment, plates were centrifuged in a Beckman GPR at 1200 rpm for five minutes at room temperature to pellet cellular debris from the conditioned media. From each well, 100 μL of conditioned media were transferred into an ELISA plate precoated with antibody 266 against βAP-13–28 (Seubert et al., supra.) and stored at 4° C. overnight. An ELISA assay employing labeled antibody 6C6 (against βAP-1–16) was run the next day to measure the amount of Aβ produced.

Cytotoxic effects of the test compounds were measured by a modification of the method of Hansen et al., (1989) J. Immun. Meth. 119:203–210. To the cells remaining in the tissue culture plate, was added 25 μL of a 3, (4,5-dimethylthiazol-2-yl)2,5-diphenyltetrazolium bromide (MTT) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% DMF, pH 4.7). Complete extraction was achieved by overnight shaking at room temperature. The difference in the $OD_{562}$ nm and the $OD_{650}$ nm was measured in a Molecular Devices $UV_{max}$ microplate reader as an indicator of the cellular viability.

The results of the Aβ ELISA were fit to a standard curve and expressed as ng/mL Aβ peptide. In order to normalize for cytotoxicity, these Aβ results were divided by the MTT results and expressed as a percentage of the results from a drug-free control.

The test compounds were assayed for Aβ production inhibition activity in cells at 10 μg/mL using the test. The results presented in Table 1 are the mean and standard deviation of at least six replicate assays. $IC_{50}$ means the concentration of test compound in micromoles/liter required to inhibit Aβ production by 50%.

TABLE 1

Aβ production inhibition activity in cells $$R^1-L^1-Y^1-\overset{\overset{Z}{\|}}{C}-Y^2-L^2-R^2$$

Aβ Production Inhibition Activity is given as an $IC_{50}$ (μM) or as a % inhibition at (@) 10 μg/ml or a given concentration of compound in μg/ml.

In each of the following compounds, $R^1$ represents 3-(4-t-butylphenoxy)phenyl, $Y^1$ represents N(OH), Z represent S and $Y^2$ represents NH.

| No. | $L^1$ | $L^2$ | $R^2$ | Inhibition |
|---|---|---|---|---|
| 1 | $CH(CH_3)$ | $CH_2$ | phenyl | 11.2 |
| 2 | $CH(CH_3)$ | $CH_2$ | 3,4-dichlorophenyl | 77% |
| 3 | $CH(CH_3)$ | $CH_2$ | 4-chlorophenyl | 11.7 |
| 4 | $CH(CH_3)$ | $CH_2$ | 4-fluorophenyl | 11.1 |
| 5 | $CH(CH_3)$ | $CH_2$ | 2-methylphenyl | 10.3 |
| 6 | $CH(CH_3)$ | $CH_2$ | 3-methylphenyl | 11.1 |
| 7 | $CH(CH_3)$ | $CH_2$ | 4-methylphenyl | 15.6 |
| 8 | $CH(CH_3)$ | $CH_2$ | 3-chloro-4-methylphenyl | 9 |
| 9 | $CH(CH_3)$ | $CH_2$ | 3,4-dimethylphenyl | 62% |
| 10 | $CH(CH_3)$ | $CH_2$ | 4-methoxyphenyl | >20 |
| 11 | $CH(CH_3)$ | $CH_2$ | 3,4-dimethoxyphenyl | 31% |
| 12 | $CH(CH_3)$ | — | 1-naphthyl | >20 |
| 13 | $CH(CH_3)$ | $CH(CH_3)$ | phenyl | 46% |
| 14 | $CH(CH_3)$ | CH(Ph) | phenyl | 44% |
| 15 | $CH(CH_3)$ | $CH_2$ | 3,4-methylenedioxyphenyl | 28% |
| 16 | $CH(CH_3)$ | $CH_2$ | 3-chlorophenyl | 12 |
| 17 | $CH(CH_3)$ | $CH_2$ | 2,4-dichlorophenyl | 5.7 |
| 18 | $CH(CH_3)$ | $CH_2$ | 3-fluorophenyl | 18.3 |
| 19 | $CH(CH_3)$ | | n-hexyl | 11 |
| 20 | $CH(C_2H_5)$ | $CH_2$ | phenyl | 3.6 |
| 21 | $CH(C_2H_5)$ | $CH_2$ | 3-methoxyphenyl | 5.6 |
| 22 | $CH(C_2H_5)$ | — | 2-chloro-3-trifluoromethylphenyl | 10% |
| 23 | $CH(C_2H_5)$ | — | 4-chloro-3-trifluoromethylphenyl | 11 |
| 24 | $CH(C_2H_5)$ | | n-hexyl | 8.8 |
| 25 | $CH(C_2H_5)$ | — | 4-(n-butoxy)phenyl | 16 |
| 26 | $CH_2$ | $CH_2$ | phenyl | 3.4 |
| 27 | $CH_2$ | | n-hexyl | 9.4 |
| 28 | $CH_2$ | $CH_2$ | 3,4-dichlorophenyl | 4.2 |
| 29 | $CH(C_3H_7)$ | $CH_2$ | phenyl | 7.5 |
| 30 | $CH(C_3H_7)$ | $CH_2$ | 3-chlorophenyl | 9.1 |
| 31 | $CH(C_3H_7)$ | $CH_2$ | 3,4-dichlorophenyl | 10 |
| 32 | $CH(C_3H_7)$ | $CH_2$ | 3-methylphenyl | 9.0 |
| 33 | CH(benzyl) | $CH_2$ | phenyl | 16% @ 5 μg/ml |
| 34 | CH(benzyl) | | n-hexyl | 20% @ 5 μg/ml |
| 35 | $CH(n-C_6H_{13})$ | — | 4-chloro-3-trifluoromethylphenyl | 9% |
| 36 | $CH(n-C_6H_{13})$ | $CH_2$ | phenyl | 26% |
| 37 | $CH(n-C_6H_{13})$ | | n-hexyl | 0% |

In each of the following compounds $R^1$ represents 3-(4-t-butylphenoxy)phenyl, Z represents S and $Y^2$ represents NH.

| No. | $L^1$ | $Y^1$ | $L^2$ | $R^2$ | Inhibition |
|---|---|---|---|---|---|
| 38 | $CH(CH_3)$ | $N(N(CH_3)_2)$ | $CH_2$ | phenyl | 32% |
| 39 | $CH(CH_3)$ | NH | $CH_2$ | phenyl | 10.5 |
| 40 | $CH_2$ | NH | $CH_2$ | phenyl | 9.1 |
| 41 | $CH_2$ | NH | $CH_2$ | 4-chloro-3-trifluoromethylphenyl | 4.0 |

TABLE 1-continued

Aβ production inhibition activity in cells $$R^1-L^1-Y^1-\overset{\overset{Z}{\|}}{C}-Y^2-L^2-R^2$$

Aβ Production Inhibition Activity is given as an $IC_{50}$ (μM) or as a % inhibition at (@) 10 μg/ml or a given concentration of compound in μg/ml.

| | | | | | |
|---|---|---|---|---|---|
| 42 | $CH_2$ | NH | | n-hexyl | 17.2 |
| 43 | $CH_2$ | $N(OCH_3)$ | | n-hexyl | 16% |
| 44 | $CH_2$ | $N(CH_3)$ | $CH_2$ | 3,4-dichlorophenyl | 40% |

In each of the following compounds $L^1$ represents $CH(CH_3)$, $Y^2$ represents NH, $L^2$ represents $CH_2$ and $R^2$ represents phenyl.

| No. | $R^1$ | $Y^1$ | Z | Inhibition |
|---|---|---|---|---|
| 45 | 3-(4-n-butylphenoxy)phenyl | N(OH) | S | 9.2 |
| 46 | 3-(4-t-butylphenoxy)phenyl | N(OH) | O | 68% |
| 47 | 3-phenoxyphenyl | NH | S | 8% |

In each of the following compounds $L^1$ represents $CH_2$, $Y^1$ represents N(OH), Z represents S and $Y^2$ represents NH.

| No | $R^1$ | $L^2$ | $R^2$ | Inhibition |
|---|---|---|---|---|
| 48 | 3-(4-t-butylbenzyloxy)phenyl | $CH_2$ | 3-methyl phenyl | 29% @ 5 μg/ml |
| 49 | 3-(4-t-butylbenzyloxy)phenyl | $CH_2$ | phenyl | 6.7 |
| 50 | 3-(4-t-butylbenzyloxy)phenyl | | n-hexyl | 25% @ 5 μg/ml |
| 51 | 3-(4-t-butylbenzyloxy)phenyl | $CH_2$ | 3,4-dichloro phenyl | 38% @ 5 μg/ml |
| 52 | 4-(4-t-butylbenzyloxy)phenyl | $CH_2$ | phenyl | 22% @ 5 μg/ml |
| 53 | 4-(4-2-phenyl-benzyloxy)phenyl | $CH_2$ | phenyl | 10% @ 5 μg/ml |
| 54 | 4-(3,4-dichloro-benzyloxy)phenyl | $CH_2$ | phenyl | 25% @ 5 μg/ml |
| 55 | 4-(3,4-dichloro-benzyloxy)phenyl | | n-hexyl | 37% @ 5 μg/ml |
| 56 | 4-(3,4-difluoro-benzyloxy)phenyl | $CH_2$ | phenyl | 28% @ 5 μg/ml |
| 57 | 4-(3,4-difluoro-benzyloxy)phenyl | | n-hexyl | 4% @ 5 μg/ml |
| 58 | 4-(2,5-dimethyl-benzyloxy)phenyl | $CH_2$ | phenyl | 32% @ 5 μg/ml |
| 59 | 4-(2,5-dimethyl-benzyloxymethyl | | n-hexyl | 28% @ 5 μg/ml |
| 60 | 4-(3,5-dimethoxy-benzyloxy)phenyl | $CH_2$ | phenyl | 17% @ 5 μg/ml |
| 61 | 4-(3,5-dimethoxy-benzyloxy)phenyl | | n-hexyl | 28% @ 5 μg/ml |
| 62 | 4-(4-n-butylbenzyl-oxy)phenyl | $CH_2$ | phenyl | 17% @ 5 μg/ml |
| 63 | 4-(4-n-butylbenzyl-oxy)phenyl | | n-hexyl | 9% @ 5 μg/ml |
| 64 | 4-(2,6-dichloro-benzyloxy)phenyl | $CH_2$ | phenyl | 18% |
| 65 | 4-(2,6-dichloro-benzyloxy)phenyl | $CH_2$ | 3-methyl phenyl | 7% |
| 66 | 3-(4-butoxybenzyl-oxy)phenyl | $CH_2$ | phenyl | 21% |
| 67 | 4-(4-acetyl-3-hydroxy-2-propy-benzyloxy)phenyl | $CH_2$ | phenyl | 42% |
| 68 | 4-(4-acetyl-3-hydroxy-2-propyl-benzyloxy)phenyl | | n-hexyl | 19.7 |
| 69 | 4-(4-benzoyl-3-hydroxy-2-propyl-benzyloxy)phenyl | — | 4-chloro-3-trifluoro-methyl-phenyl | 14% |
| 70 | 3-(3-hydroxy-4-propanoyl-2-propyl-benzyloxy)phenyl | | n-hexyl | 37% |
| 71 | 3-(3-hydroxy-4-propanol-2-propyl-benzyloxy)phenyl | $CH_2$ | phenyl | 12.0 |
| 72 | 3-(3,5-di-t-butyl-4-methoxybenzyl-oxy)phenyl | $CH_2$ | phenyl | 8.1 |
| 73 | 4-(3,5-di-t-butyl-4-methoxybenzyloxy)phenyl | $CH_2$ | phenyl | 5.9 |
| 74 | 2-and-4-(2-phenyl-benzyloxy)phenyl | $CH_2$ | phenyl | 7.1 (mixture) |

In the following compounds $L^1$ represents $CH(CH_3)$, $Y^1$ represents N(OH), Z represents S and $Y^2$ represents NH.

| No. | $R^1$ | $L^2$ | $R^2$ | Inhibition |
|---|---|---|---|---|
| 75 | 3-(4-t-butylbenzyloxy)phenyl | $CH_2$ | phenyl | 8.9 |

In the following compounds, $L^1$ represents $CH_2$, $Y^1$ represents N(OH), Z represents S and $Y^2$ represents NH.

| No. | $R^1$ | $L^2$ | $R^2$ | Inhibition |
|---|---|---|---|---|
| 76 | 4-biphenyl | $CH_2$ | 3,4-dichloro phenyl | 13% |
| 77 | 4-biphenyl | $CH_2$ | phenyl | 2% @ 5 μg/ml |
| 78 | 4-biphenyl | | n-hexyl | 24% @ 5 μg/ml |
| 79 | 4-biphenyl | $CH_2$ | 3-methyl phenyl | 15% |
| 80 | 4-(4-t-butylphenyl)phenyl | | n-hexyl | 11% |
| 81 | 4-(4-t-butylphenyl)phenyl | $CH_2$ | phenyl | 20% |
| 82 | 4-(4-t-butylphenyl)phenyl | $CH_2$ | 3-methyl phenyl | 30% |
| 83 | 4-(4-t-butylphenyl)phenyl | — | 4-chloro-3-trifluoro-methyl-phenyl | 12.4 |
| 84 | 3-(4-t-butyl-benzamido)-phenyl | $CH_2$ | phenyl | 15 |
| 85 | 3-(4-t-butyl-benzamido)-phenyl | | n-hexyl | 18.6 |
| 86 | 3-(4-t-butyl-phenylthio)phenyl | $CH_2$ | phenyl | 5.9 |
| 87 | 3-(4-t-butyl-phenylthio)phenyl | | n-hexyl | 9.9 |
| 88 | 4-(4-t-butyl-phenylthio)phenyl | $CH_2$ | phenyl | 7.5 |
| 89 | 4-(4-t-butyl-phenylthio)phenyl | | n-hexyl | 5.3 |
| 90 | 3-(4-t-butyl-phenyl | | n-hexyl | 22 |

TABLE 1-continued

Aβ production inhibition activity in cells $$R^1-L^1-Y^1-\overset{\overset{Z}{\|}}{C}-Y^2-L^2-R^2$$

Aβ Production Inhibition Activity is given as an IC$_{50}$ (μM) or as a % inhibition at (@) 10 μg/ml or a given concentration of compound in μg/ml.

| No. | R¹ | L² (or middle) | R² | Inhibition |
|---|---|---|---|---|
| | sulphonyl)phenyl | | | |
| 91 | 3-(4-t-butyl-phenyl-sulphinyl)phenyl | CH₂ | phenyl | 17.1 |
| 92 | 3-(4-t-butyl-phenyl-sulphonyl)phenyl | CH₂ | phenyl | 25% |
| 93 | 3-(4-t-butyl-phenyl-sulphonyl)phenyl | | n-hexyl | 13% |
| 94 | 4-(4-t-butyl-phenylthiomethyl)phenyl | CH₂ | phenyl | 13.1 |
| 95 | 4-(4-t-butyl-phenylthiomethyl)phenyl | — | 4-chloro-3-trifluoromethylphenyl | 4.6 |
| 96 | 4-(4-1,1-dimethylpropylphenoxymethyl)phenyl | | n-hexyl | 24.8 |
| 97 | 4-(4-1,1-dimethylpropylphenoxymethyl)phenyl | CH₂ | phenyl | 10.0 |

In the following compounds L¹ represents CH(CH₃), Y¹ represents N(OH), Z represents S and Y² represents NH.

| No. | R¹ | L² | R² | Inhibition |
|---|---|---|---|---|
| 98 | 3-(4-t-butyl-benzamido)phenyl | | n-hexyl | 13 |
| 99 | 3-(4-t-butyl-benzamido)phenyl | CH₂ | phenyl | 43% @ 5 μg)ml |
| 100 | 3-(4-t-butyl-benzamido)phenyl | CH₂ | 3-methylphenyl | 1% @ 5 μg)ml |

In the following compounds, L¹ represents CH₂, Y¹ represents N(OH) and Y² represents NH.

| No. | R¹ | Z | L² | R² | Inhibition |
|---|---|---|---|---|---|
| 101 | 3-(2-propyl-4-t-butylphenoxy)phenyl | S | CH₂ | phenyl | 4.5 |
| 102 | 3-(2-propyl-4-t-butylphenoxy)phenyl | S | | n-hexyl | 6.1 |
| 103 | 3-(2-propyl-4-t-butylphenoxy)phenyl | O | | 4-chloro-3-CF₃-phenyl | 20 |

In each of the following compounds, R¹ represents 4-(4-t-butylphenoxyphenyl), L¹ represents a bond, Y¹ represents NH, Z represents S and Y² represents NH.

| No. | L² | R² | Inhibition |
|---|---|---|---|
| 104 | CH₂ | 2-chlorophenyl | 13.4 |
| 105 | CH₂ | 3-chlorophenyl | 9.4 |
| 106 | CH₂ | 4-chlorophenyl | 9.2 |
| 107 | CH₂ | 3-bromophenyl | 7.2 |
| 108 | CH₂ | 4-bromophenyl | 8.9 |
| 109 | CH₂ | 2-methoxyphenyl | 37% |
| 110 | CH₂ | 3-methoxyphenyl | 21.2 |
| 111 | CH₂ | 4-methoxyphenyl | 8.30 |
| 112 | CH₂ | 3-fluorophenyl | 7.60 |
| 113 | CH₂ | 4-fluorophenyl | 5.60 |
| 114 | — | phenyl | 18.2 |
| 115 | CH₂ | phenyl | 16.4 |
| 116 | (CH₂)₂ | phenyl | 19.8 |
| 117 | (CH₂)₃ | phenyl | 17.0 |
| 118 | (CH₂)₄ | phenyl | 16.4 |
| 119 | — | cyclohexyl | 15.2 |
| 120 | CH₂ | 2-pyridyl | 15.6 |
| 121 | CH₂ | 3-pyridyl | 37% |
| 122 | CH₂ | 4-pyridyl | 23.5 |
| 123 | (CH₂)2 | 2-pyridyl | 12.3 |
| 124 | CH₂ | n-t-butoxycarbonyl-2-piperidinyl | 31% |
| 125 | CH₂ | n-t-butoxycarbonyl-3-piperidinyl | 9.30 |
| 126 | CH₂ | 2-piperidinyl | 7.00 |
| 127 | CH₂ | 3-piperidinyl | 11.7 |
| 128 | CH₂ | 2,4-difluorophenyl | 7.3 |
| 129 | CH₂ | 3,4-difluorophenyl | 4.5 |
| 130 | CH₂ | 2-chloro-4-fluorophenyl | 7.2 |
| 131 | CH₂ | 3-chloro-4-fluorophenyl | 5.0 |
| 132 | CH₂ | 4-fluoro-2-trifluoromethyl-phenyl | 8.0 |
| 133 | CH₂ | 3,4-dichlorophenyl | 6.5 |
| 134 | CH₂ | 2-trifluoromethyl-1,3,4-thiadiazolyl | 10.2 |
| 135 | | n-hexyl | 10.6 |

In each of the following compounds, L¹ represemts a bond, Y¹ represents NH, Y² represents NH and L² represents a bond.

| No. | R² | R¹ | Z | Inhibition |
|---|---|---|---|---|
| 136 | 3,4-dichlorophenyl | 5-quinolinyl | O | 17.8 |
| 137 | 3,4-dichlorophenyl | 2-benzothiazolyl | O | 10.3 |
| 138 | 3,4-dichloro-phenyl | 2-pyrimidinyl | O | 7% |
| 139 | 3,4-dichlorophenyl | 4-chlorophenyl | S | 6.6 |
| 140 | 3,4-dichlorophenyl | 2-benzimidazolyl | O | 17.4 |
| 141 | 3,4-dichlorophenyl | 2-dimethylaminopropyl thiophenyl | O | 7.5 |
| 142 | 3,4-dichlorophenyl | 2-methoxycarbonyl-phenyl | O | 22% |
| 143 | 3,4-dichlorophenyl | 2-(5,6-dimethyl)benzimidazolyl | O | 14.9 |
| 144 | 3,4-dichlorophenyl | 2,4-dimethoxyphenyl | O | 41% |
| 145 | 3,4-dichlorophenyl | 4-(3,4-dichlorophenyl)thiophenyl | O | 6.2 |
| 146 | 3,4-dichlorophenyl | benzyl | S | 21.8 |
| 147 | 3,4-dichlorophenyl | 3-trifluoromethyl phenyl | S | 4.7 |
| 148 | 3,4-dichlorophenyl | 4-phenoxyphenyl | S | 7.5 |
| 149 | 3,4-dichlorophenyl | 4-methylthiophenyl | O | 13.8 |
| 150 | 3,4-dichlorophenyl | 3-bromo-4-methylthiophenyl | O | 5.2 |
| 151 | 3,4-dichlorophenyl | 2-chlorophenyl | O | 10.1 |

TABLE 1-continued

Aβ production inhibition activity in cells $$R^1-L^1-Y^1-\overset{\overset{Z}{\|}}{C}-Y^2-L^2-R^2$$

Aβ Production Inhibition Activity is given as an IC$_{50}$ (μM) or as a % inhibition at (@) 10 μg/ml or a given concentration of compound in μg/ml.

| No. | R$^1$ | | | Inhibition |
|---|---|---|---|---|
| 152 | 3,4-dichlorophenyl | phenyl | O | 11.4 |
| 153 | 3,4-dichlorophenyl | 3,4-dichlorophenyl | S | 1.7 |
| 154 | 3,4-dichlorophenyl | 4-methylthiophenyl | O | 8.6 |
| 155 | 3,4,5-trichlorophenyl | 4-methylthiophenyl | O | 5.8 |
| 156 | 4-chlorophenyl | 4-methylthiophenyl | O | 13% |
| 157 | 2-chlorophenyl | 4-methylthiophenyl | O | 41% |
| 158 | 2,3-dichlorophenyl | 4-methylthiophenyl | O | 51% |
| 159 | 2,4-dichlorophenyl | 4-methylthiophenyl | O | 4% |
| 160 | 4,5-dichloro-2-methylphenyl | 4-methylthiophenyl | O | 48% |
| 161 | 4-chlorophenyl | 4-methylsulfonylphenyl | O | 40% |
| 162 | 3-chlorophenyl | 3-bromo-4-methylthiophenyl | O | 5.7 |
| 163 | 3-chlorophenyl | 2,5-dichloro-4-methylthiophenyl | O | 10.5 |
| 164 | 4-methylthiophenyl | 3-bromo-4-methylthiophenyl | O | 14.4 |
| 165 | 4-chloro-3-CF$_3$-phenyl | 3-methoxy-4-methoxycarbonylphenyl | O | 42% |
| 166 | 4-chloro-3-CF$_3$-phenyl | 4-chloro-3-trifluoromethylphenyl | S | 2.8 |
| 167 | 4-chloro-3-CF$_3$-phenyl | 4-chloro-3-trifluoromethylphenyl | O | 1.4 |

In each of the following compounds, Z represents S, Y$^2$ represents NH, L$^2$ represents a bond and R$^2$ represents 4-chloro-3-trifluoromethylphenyl.

| No. | R$^1$ | L$^1$ | Y$^1$ | Inhibition |
|---|---|---|---|---|
| 167 | 4-(4-t-butylphenoxy)phenyl | — | NH | 3.3 |
| 168 | 3-(4-t-butylphenoxy)phenyl | — | NH | 3.9 |
| 169 | 4-(3-t-butylphenoxy)phenyl | — | NH | 4.6 |
| 170 | 2-(4-t-butylphenoxy)phenyl | — | NH | 4.4 |
| 171 | 2-(4-t-butylphenoxy)phenyl | — | N(OH) | 10.8 |
| 172 | 3-(3-t-butylphenoxy)phenyl | — | NH | 3.8 |
| 173 | 3-(3-t-butylphenoxy)phenyl | — | N(OH) | 2.8 |
| 174 | 4-(2-t-butylphenoxy)phenyl | — | NH | 66% |

In each of the following compounds, L$^1$ represents a bond, Y$^1$ represents NH, Z represents S, Y$^2$ represents NH and R$^2$ represents 3-trifluoromethylphenyl.

| No. | R$^1$ | L$^2$ | Inhibition |
|---|---|---|---|
| 175 | 4-(4-t-butylphenoxy)phenyl | — | 7.3 |
| 176 | 4-(3-t-butylphenoxy)phenyl | — | 4.6 |
| 177 | 4-(2-t-butylphenoxy)phenyl | — | 7.6 |
| 178 | 4-(3-t-butylphenoxy)phenyl | CH$_2$ | 8.6 |
| 179 | 4-(4-t-butylphenoxy)phenyl | CH$_2$ | 6.5 |

In each of the following compounds, R$^1$ represents 2-(4-t-butylphenoxyphenyl), Z represents S, and Y$^2$ represents NH.

| No. | L$^1$ | Y$^1$ | L$^2$ | R$^2$ | Inhibition |
|---|---|---|---|---|---|
| 180 | CH$_2$ | N(OH) | CH$_2$ | phenyl | 11.6 |
| 181 | — | NH | CH$_2$ | phenyl | 52% |
| 182 | CH$_2$ | N(OH) | — | n-hexyl | 34 |
| 183 | — | NH | CH$_2$ | 3,4-dichlorophenyl | 24% |
| 184 | — | NH | CH$_2$ | 3,4-dimethylphenyl | 36% |
| 185 | — | NH | — | n-hexyl | 21% |

In each of the following compounds Z represents S, Y$^2$ represents NH, L$^2$ represents CH$_2$ and R$^2$ represents phenyl.

| No. | R$^1$ | L$^1$ | Y$^1$ | Inhibition |
|---|---|---|---|---|
| 186 | 3-(4-t-butylphenoxy)phenyl | — | NH | 9.0 |
| 187 | 3-(3-t-butylphenoxy)phenyl | CH$_2$ | N(OH) | 12.1 |
| 188 | 4-(2-t-butylphenoxy)phenyl | — | NH | 9.4 |

In each of the following compounds L$^1$ represents a bond, Y$^1$ represents NH, Z represents S, Y$^2$ represents NH, L$^2$ represents a bond a R$^2$ represents 2-trifluoromethyl-phenyl.

| No. | R$^1$ | Inhibition |
|---|---|---|
| 189 | 4-(3-t-butylphenoxy)phenyl | 37% |
| 190 | 4-(2-t-butylphenoxy)phenyl | 13.8 μM |

In each of the following compounds L$^1$ represents a bond, Y$^1$ represents NH, Z represents S, Y$^2$ NH, L$^2$ represents a bond and R$^2$ represents 4-chlorophenyl.

| No. | R$^1$ | Inhibition |
|---|---|---|
| 191 | 4-(4-t-butylphenoxy)phenyl | 33% |
| 192 | 3-(4-t-butylphenoxy)phenyl | 8.8 |

In each of the following compounds R$^1$ represents 4-(4-t-butyl-2-propyl)phenoxyphenyl, L$^1$ represents a bond, Y$^1$ represents NH, Z represents S and Y$^2$ NH.

| No. | L$^2$ | R$^2$ | Inhibition |
|---|---|---|---|
| 193 | — | 4-chloro-3-trifluoromethylphenyl | 29% |
| 194 | CH$_2$ | 3-methylphenyl | 31% |
| 195 | — | 3-trifluoromethylphenyl | 11 |
| 196 | — | 3,4-dimethylphenyl | 44% |
| 197 | CH$_2$ | phenyl | 4.6 |

In each of the following compounds, Z representsd S, Y$^2$ represents NH, L$^2$ represents CH$_2$ and R$^2$ represents phenyl.

| No. | R$^1$ | L$^1$ | Y$^1$ | Inhibition |
|---|---|---|---|---|
| 198 | 4-(4-t-butylphenoxy)phenyl | CH$_2$ | S | 10 |
| 199 | 4-acetyl-3-hydroxy-2-propylphenyl | CH$_2$ | S | 2 |
| 200 | 3,4-dichlorophenyl | — | NH | 21.8 |

In each of the following compounds R$^1$ represents 4-benzoyl-3-hydroxy-2-propylphenyl, L$^1$ represents a bond, Y$^1$ represents NH, Z represents S and Y$^2$ represents NH.

| No. | L$^2$ | R$^2$ | Inhibition |
|---|---|---|---|
| 201 | — | 3-trifluoromethylphenyl | 20 |
| 202 | — | n-hexyl | 42% |
| 203 | — | 4-t-butylphenyl | 2% |

In each of the following compounds L$^1$ represents a bond, Y$^1$ represents NH, Y$^2$ represents NH, L$^2$ represents a bond and R$^2$ represents 4-chloro-3-trifluoromethylphenyl.

| No. | R$^1$ | Z | Inhibition |
|---|---|---|---|
| 204 | 4-(2-quinolylthio)phenyl | S | 3.7 |
| 205 | 4-(4-ethoxycarbonyl-2-quinolylthio)phenyl | S | 3.1 |
| 206 | 4-(6-chloro-2-quinolylthio)phenyl | S | 2.7 |

TABLE 1-continued

Aβ production inhibition activity in cells $$R^1-L^1-Y^1-\overset{\overset{Z}{\|}}{C}-Y^2-L^2-R^2$$

Aβ Production Inhibition Activity is given as an IC$_{50}$ (μM) or as a % inhibition at (@) 10 μg/ml or a given concentration of compound in μg/ml.

| 207 | 4-(4-phenyl-2-quinolylthio)phenyl | S | >20 |
| 208 | 4-(6-methoxy-2-quinolylthio)phenyl | S | 4.4 |
| 209 | 4-(4-quinolylthio)phenyl | S | 4.7 |
| 210 | 4-(7-trifluoromethyl-4-quinolylthio)phenyl | S | 4.5 |
| 211 | 4-(2-naphthylthio)phenyl | S | 2.6 |
| 212 | 4-(1-naphthylthio)phenyl | S | 4.9 |
| 213 | 4-(2-benzimidazolylthio)phenyl | S | 7.1 |
| 214 | 4-(2-benzoxazolylthio)phenyl | S | 12.5 |
| 215 | 4-(2-benzothiazolylthio)phenyl | S | 3.9 |
| 216 | 4-(5-chloro-2-benzothiazoylthio)phenyl | S | 1.7 |
| 217 | 4-(2-quinolylsulfinyl)phenyl | S | 12.1 |
| 218 | 4-(2-quinolylsulfonyl)phenyl | S | 3.7 |
| 219 | 4-(2-quinolylamino)phenyl | S | 11.8 |
| 220 | 4-(2-quinolyloxy)phenyl | S | 9.7 |
| 221 | 4-(2-quinolylthio)phenyl | O | >20 |
| 222 | 4-(6-phenyl-3-pyridazylthio)phenyl | S | 4.4 |
| 223 | 4-(2-pyridazylthio)phenyl | S | 8.3 |
| 224 | 4-(5-nitroquinolylthio)phenyl | S | 4.3 |
| 225 | 4-(4-isopropylsulfonyl)phenyl | S | 3.3 |

In each of the following compounds L$^1$ represents a bond, Y$^1$ represents NH, Y$^2$ represents NH, L$^2$ represents a bond and R$^2$ represents 3,4-dichlorophenyl.

| No. | R$^1$ | Z | Inhibition |
| --- | --- | --- | --- |
| 226 | 4-(2-quinolythio)phenyl | S | 13.8 |

In each of the following compounds L$^1$ represents a bond, Y$^1$ represents a bond, Z represents O, Y$^2$ represents NH, L$^2$ represents a bond and R$^2$ represents 3,4-dichlorophenyl.

| No. | R$^1$ | Inhibition |
| --- | --- | --- |
| 227 | 2-pyridyl | 32% |
| 228 | 6-1,2,5-triazinyl | 22% |
| 229 | 1-piperidinyl | 8% |
| 230 | 1-ethyl-3-piperidinyl | 28% |
| 231 | 2,2,6,6-tetramethyl-4-piperidinyl | 40–51% @ 2.5 μg/ml |
| 232 | 5-chloro-1,3,4-thiadiazol-2-yl | 2.0 |
| 233 | 2-methoxycarbonylbenzothiophen-3-yl | 15.2 |
| 234 | 5-methyl-1,3,4-thiadiazol-2-yl | 5.0 |
| 235 | 1,3,4-thiadiazol-2-yl | 10.0 |
| 236 | 5-trifluoromethyl-1,3,4-thiadiazol-2-yl | 4.2 |
| 237 | 5-t-butyl-1,3,4-thiadiazol-2-yl | 2.9 |
| 238 | 5-(2-chloro-1,1-dimethylethyl)-1,3,4-thiadiazol-2-yl | 1.4 |
| 239 | 5-hexylthio-1,3,4-thiadiazol-2-yl | 1.4 |
| 240 | 5-bromo-1,3,4-thiadiazol-2-yl | 1.8 |
| 241 | 2-oxazolyl | −8% |
| 242 | 5-methylisoxazol-3-yl | 29% |
| 243 | 2-thiazolyl | 19.4 |
| 244 | 4,5-dihydrothiazolyl | 10% |
| 245 | 3-t-butylisoxazol-5-yl | 9.8 |
| 246 | 3-t-butyl-1,2,4-oxadiazol-5-yl | 5.8 |
| 247 | 3-trifluoromethyl-1,2,4-oxadiazol-5-yl | 4.4 |

In each of the following compounds, R$^1$ represents 5-methyl-1,3,4-thiadiazol-2-yl, L$^1$ represents a bond, Y$^1$ represents NH, Z represents O, Y$^2$ represents NH and L$^2$ represents a bond.

| No. | R$^2$ | Inhibition |
| --- | --- | --- |
| 248 | 3-chlorophenyl | 47% |
| 249 | 2-fluorophenyl | 6% |
| 250 | 3-chloro-4-fluorophenyl | 9.8 |
| 251 | 2,6-dimethylphenyl | −13% |
| 252 | 3-methylthiophenyl | 25% |

In each of the following compounds R$^1$ represents 5-bromo-1,3,4-thiadiazol-2-yl, L$^1$ represents a bond, Z represents O, Y$^2$ represents NH and L$^2$ represents a bond.

| No. | Y$^1$ | R$^2$ | Inhibition |
| --- | --- | --- | --- |
| 253 | NH | methyl | 2% |
| 254 | N(CH$_3$) | methyl | 11% |

In each of the following compounds, R1 represents 1,3,4-thiadiazol-2-yl, L$^1$ represents a bond, Y$^1$ represents NH, Z represents O, Y$^2$ represents NH and L$^2$ represents a bond.

| No. | R$^2$ | Inhibition |
| --- | --- | --- |
| 255 | phenyl | 1% |
| 256 | 4-chlorophenyl | 42% |

The compounds of the present invention can be administered for prophylactic and/or therapeutic treatment of diseases related to the deposition of Aβ, such as Alzheimer's disease, Down's syndrome, and advanced aging of the brain. In therapeutic applications, the compounds are administered to a host already suffering from the disease. The compounds will be administered in an amount sufficient to inhibit further deposition of senile plaques. The specific dose of compound administered according to this invention to obtain therapeutic and/or prophylactic effects will, of course, be determined by the particular circumstances surrounding the case, including, for example, the compound administered, the route of administration, the condition being treated, the individual being treated and the like. A typical daily dose will contain a dosage level of from about 0.01 mg/kg to about 50 mg/kg of body weight of an active compound of this invention. Preferred daily doses generally will be from about 0.05 mg/kg to about 20 mg/kg, for example from about 0.1 mg/kg to about 10 mg/kg.

For prophylactic applications, the compounds of the present invention are administered to a warm-blooded mammal susceptible to Alzheimer's Disease or a βAP-related disease, but not already suffering from such disease. Such hosts may be identified by genetic screening and clinical analysis, as described in the medical literature. See e.g., Goate, (1991) Nature 349:704–706. The compounds will be able to inhibit or prevent the formation of senile plaques at a symptomatically early stage, preferably preventing even the initial stages of the μamyloid disease.

The compounds can be administered by a variety of routes including oral, rectal, transdermal, subcutaneous, intravenous, intramuscular and intranasal. The compounds of the present invention are preferably formulated prior to administration.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

For example, a typical pharmaceutical composition for intramuscular injection would contain about one $\mu$g to one mg of the compound in from one to four milliliters of sterile buffered water. The typical pharmaceutical composition for intravenous infusion would contain about one to one hundred milligrams of the compound in from one hundred to five hundred milliliters of sterile Ringer's solution.

The pharmaceutical formulations are prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight % |
|---|---|
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formuation 4
Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| | |
|---|---|
| Active Ingredient | 80 mg |
| Starch | 59 mg |

Formulation 5
Capsules each containing 80 mg medicament are made as follows:

| | |
|---|---|
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| | |
|---|---|
| Active Ingredient | 225 mg |
| | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| | |
|---|---|
| Active Ingredient | 100 mg |
| Mannitol | 100 mg |
| 5 N Sodium hydroxide | 200 ml |
| Purified water to total | 5 ml |

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportation across the blood-brain barrier. Alternatively, the delivery of hydrophilic drugs can be enhanced by intra-arterial infusion of hypertonic solutions which can transiently open the blood-brain barrier.

The following examples illustrate the invention:

In this specification, the following abbreviations have been used. THF refer to tetrahydrofuran, DMF refers to dimethylformamide, HPLC refers to high pressure liquid chromatography, DMAP refers to 4-dimethylaminopyridine, and DBU refers to 1,8-diazabicyclo[5,4,0]undec-7-ene.

General Procedures

In each of the following examples, one of the following three general procedures was used.

Procedure A. An amine (1 equivalent), isothiocyanate (1 equivalent), and 4-dimethylaminopyridine (1.1 equivalent) were dissolved in THF (2.5 ml/mmole) and stirred for 16 hr at room temperature under an atmosphere of nitrogen. The solution was concentrated in vacuo, ethyl acetate added, and washed twice with water. The organic layer was dried over sodium sulfate and condensed. The thiourea was purified by HPLC over silica gel eluted with 30% ethyl acetate/hexane.

Procedure B. An amine (1 equivalent), isothiocyanate (1 equivalent), and potassium carbonate (1 equivalent) were dissolved in THF (2.5 ml/mmole) and refluxed for 3 hr. The cooled solution was concentrated, ethyl acetate added, washed with water, dried over sodium sulfate and condensed. The product was purified by HPLC over silica gel eluted with ethyl acetate/hexane.

Procedure C. An amine (1 equivalent) and isothiocyanate (1 equivalent) were dissolved in THF (2.5 ml/mmole) and stirred at room temperature for 16 hr. The solution was concentrated, ethyl acetate added, washed with water, dried over sodium sulfate, and concentrated. The product was purified by HPLC over silica gel eluted with ethyl acetate/hexane.

EXAMPLE 1

1-[4-(2-quinolyl)thiophenyl]-3-(4-chloro-3-trifluoromethylphenyl)thiourea 2-(4-aminophenylthio)quinoline(3.9 mmoles, 1.0 g) and 4-chloro-3-trifluoromethylphenylisothiocyanate (3.9 mmoles, 0.92 g) were reacted according to procedure A to yield 1.06 g, 56% of the title compound. Mass spec (FD) 490. Calculated for $C_{23}H_{15}ClF_3N_3S_2$: C, 56.38; H, 3.09, N, 8.58. Found: C, 56.60; H, 3.11; N, 8.42.

The necessary amine starting material was prepared as follows:

2-Chloroquinoline (0.04 moles, 6.54 g), 4-aminothiophenol (0.04 moles, 5.0 g) and potassium carbonate (0.04 moles, 5.52 g) were stirred at room temperature in 200 ml of ethanol for 18 hr. The reaction mixture was concentrated, ethyl acetate was added and the solution washed with water, dried over sodium sulfate and concentrated. The product was purified by HPLC over silica gel eluted with ethyl acetate/hexane to yield 2-(4-aminophenylthio)quinoline 4.0 g, 40%. Mass Spec (FD) 252. Calculated for $C_{15}H_{12}N_2S$: C, 71.40; H, 4.79, N, 11.10. Found: C, 71.11; H, 4.98N, 11.20.

EXAMPLE 2

1-[4-(4-ethoxycarbonyl-2-quinolylthio)phenyl]-3-(4-chloro-3-trifluoromethylphenyl)thiourea 2-(4-aminophenylthio)-4-ethoxycarbonylquinoline (6.0 mmoles, 2.0 g) and 4-chloro-3-trifluoromethylphenylisothiocyanate (6.0 mmoles, 1.4 g) were reacted according to procedure C to yield 3.0 g, 89% of the title compound. Mass Spec (FD) 561. Calculated for C$_{26}$H$_{19}$ClF$_3$N$_3$O$_2$S$_2$: C, 55.56; H, 3.41; N, 7.48. Found: C, 55.38H, 3.38; N, 7.36.

The necessary amine stating material was prepared as follows:

2-Chloro-4-ethoxycarbonylquinoline (0.024 moles, 5.56 g), 4-aminothiophenol (0.024 moles, 3.0 g) and 4-dimethylaminopyridine (0.024 moles, 2.9 g) were stirred in 250 ml ethanol for 3 days.

The reaction mixture was filtered, concentrated, ethyl acetate added, washed with water and dried over sodium sulfate. The solution was concentrated and the product purified by HPLC over silica gel eluted with 25% ethyl acetate/hexane to yield 2-(4-aminophenylthio)-4-ethoxycarbonylquinoline 2.8 g, 36%. (FD) 324. Calculated for C$_{18}$H$_{16}$N$_2$O$_2$S: C, 66.64; H, 4.97; N, 8.63. Found: C, 66.50; H, 5.00N, 8.54.

EXAMPLE 3

1-[4-(6-Chloro-2-quinolylthio)phenyl]-3-(4-chloro-3-trifluoromethylphenyl)thiourea 2-(4-Aminophenylthio)-6-chloroquinoline (2.9 mmoles, 0.83 g) and 4-chloro-3-trifluoromethylphenylisothiocyanate (3.2 mmoles, 0.76 g) were reacted according to procedure C to yield 0.78 g, 51% of the title compound. Mass Spec (FD) 524. Calculated for C$_{23}$H$_{14}$ClF$_3$N$_3$S$_2$: C, 52.68; H, 2.69; N, 8.01. Found: C, 52.66; H, 2.78; N, 7.91. M Pt 138°–1390° C.

The necessary amine starting material was prepared as follows:

2,6-Dichloroquinoline (15.2 mmoles, 3.0 g), 4-aminothiophenol (15.2 mmoles, 1.9 g), and DMAP 15.2 mmoles, 1.85 g) were stirred at room temperature for 3 days. The solvent was removed, diluted with ethyl acetate, washed with water, dried over sodium sulfate and concentrated. The product was purified by HPLC over silica gel eluted with 25% ethyl acetate in hexane to yield 2-(4-aminophenylthio)-6-chloroquinoline 830 mg, 19%. Mass spec (FD) 286. Calculated. for C$_{15}$H$_{11}$ClN$_2$S: C, 62.82H, 3.87; N, 9.77. Found: C, 63.09; H, 3.94; N, 9.61.

EXAMPLE 4

1-[4-(4-Phenyl-2-quinolylthio)phenyl]-3-(4-chloro-3-trifluoromethyl-phenyl)thiourea 2-(4-aminophenylthio)-4-phenylquinoline (3.0 mmoles, 1.0 g) and 4-chloro-3-trifluoromethylphenylisothiocyanate (3.3 mmoles, 0.79 g) were reacted according to procedure C to yield the title compound 1.03 g, 61%. Mass Spec (FD) 565. Calculated for C$_{29}$H$_{19}$ClF$_3$N$_3$S$_2$: C, 61.53; H, 3.38; N, 7.42. Found: C, 61.82; H, 3.63; N, 7.43.

The necessary amine starting material was prepared as follows:

2-Chloro-4-phenylquinoline (4.18 mmoles, 10.0 g), 4-aminothiophenol (41.8 mmoles, 5.2 g) and DMAP (41.8 mmoles, 5.0 g) were stirred in 200 ml ethanol and 50 ml THF for 3 days. The solution was concentrated, ethyl acetate added, washed with water, dried over sodium sulfate and the solvent removed. The product was purified by HPLC over silica gel eluted with 30% ethyl acetate in hexane to yield 2-(4-aminophenylthio)-4-phenylquinoline 6.2 g, 45%. Mass Spec (FD) 328. Calculated for C$_{21}$H$_{16}$N$_2$S: C, 76.80; H, 4.91N, 8.53. Found: C, 77.04; H, 5.00; N, 8.55.

EXAMPLE 5

1-[4-(6-Methoxy-2-quinolylthio)phenyl]-3-(4-chloro-3-trifluoromethylphenyl)thiourea 2-(4-aminophenylthio)-6-methoxyquinoline 15.0 mmoles, 4.2 g) and 4-chloro-3-trifluoromethylphenylisothiocyanate 15.0 mmoles, 3.6 g) were reacted according to procedure C to yield 5.6 g, 72% of the title compound. Mass Spec (FD) 519. Calculated for C$_{24}$H$_{17}$ClF$_3$N$_3$OS$_2$: C, 55.44; H, 3.30; N, 8.08. Found: C, 55.62; H, 3.43; N, 8.27.

The necessary amine starting material was prepared as follows:

2-Chloro-6-methoxyquinoline (52.0 mmoles, 10.0 g), 4-aminothiophenol (52.0 mmoles, 6.5 g) and dimethylaminopyridine (52.0 mmoles, 6.3 g) were stirred for 16 hr in 250 ml ethanol. The reaction was condensed and purified by HPLC over silica gel eluted with 25–30% ethyl acetate/hexane to yield 2-(4-aminophenylthio)-6-methoxyquinoline. 8.5 g, 58% product. Mass spec (FD) 282. Calculated for C$_{16}$H$_{14}$N$_2$OS: C, 68.06; H, 5.00, N, 9.92. Found: C, 68.04; H, 4.97; N, 10.02.

EXAMPLE 6

1-[4-(4-Quinolylthio)Phenyl]-3-(4-chloro-3-trifluoromethylphenyl)thiourea 4-(4-aminophenylthio)quinoline (3.9 mmoles, 1.0 g) and 4-chloro-3-trifluoromethylphenylisothiocyanate (3.9 mmoles, 0.92 g) were reacted according to procedure A to yield of the title compound 1.06 g, 56%. Mass spec (FD) 490. Calculated for C$_{23}$H$_{15}$ClF$_3$N$_3$S$_2$: C, 56.38; H, 3.09, N, 8.58. Found: C, 56.60; H, 3.11; N, 8.42.

The necessary amine starting material was prepared as follows:

a) 4-Chloroquinoline (32.3 mmoles, 5.2 g), 4-nitrothiophenol (32.3 mmoles, 5.0 g) and potassium carbonate (32.3 mmoles, 4.46 g) were stirred at room temperature in 500 ml of ethanol for 16 hr. The reaction mixture was then concentrated, ethyl acetate was added and the solution washed with water, dried over sodium sulfate and concentrated. The product was purified by HPLC over silica gel eluted with 20–40% ethyl acetate/hexane to yield 4-(4-nitrophenylthio)quinoline 4.9 g, 54%. Mass Spec (FD) 282. Calculated for C$_{15}$H$_{10}$N$_2$O$_2$S: C, 63.82H, 3.57N, 9.92. Found: C, 65.09; H, 3.81; N, 10.02.

b) 4-(4-nitrophenylthio)quinoline 17.0 mmoles, 4.9 g) was dissolved in 200 ml ethanol and hydrogenated over 5 g of 5% Pd/C at 40 psi for 1 hr at room temperature. The solution was filtered through celite and the solvent removed to yield 4-(4-aminophenylthio)quinoline 2.5 g, 58%. Mass spec (FD) 253. Calculated for C$_{15}$H$_{12}$N$_2$S: C, 71.40; H, 4.79, N, 11.10. Found: C, 71.12; H, 4.93N, 10.88.

EXAMPLE 7

1-[4-(7-Trifluoromethyl-4-quinolylthio)phenyl]-3-(4-chloro-3-trifluoromethylphenyl)thiourea 4-(4-aminophenylthio)-7-trifluoromethylquinoline (0.01 mole, 3.2 g) and 4-chloro-3-trifluoromethylphenylisothiocyanate (0.01 mole, 2.4 g) were reacted according to procedure C to yield the title compound 3.5 g, 63%. Mass Spec (FD) 557. Calculated for C$_{24}$H$_{14}$ClF$_6$N$_3$S$_2$: C, 51.66; H, 2.53; N, 7.53. Found: C, 51.92; H, 2.53; N, 7.46.

The necessary amine starting material was prepared as follows:

4-Chloro-7-trifluoromethylquinoline (0.043 moles, 10.0 g), 4-aminothiophenol (0.043 moles, 5.3 g) and 4-dimethylaminopyridine (0.04 moles, 4.9 g) were stirred in 250 ml ethanol for 3 days. The reaction mixture was filtered, concentrated, ethyl acetate added, washed with water and dried over sodium sulfate. The solution was concentrated and the product purified by HPLC over silica gel eluted with 25% ethyl acetate/hexane to yield 4-(4-aminophenylthio)-7-trifluoromethylquinoline 10.2 g, 74%. Mass Spec (FD) 320. Calculated for $C_{16}H_{11}F_3N_2S$: C, 59.99; H, 3.46; N. 8.74. Found: C, 60.08; H, 3.49; N, 8.77.

EXAMPLE 8

1-[4-(2-Naphthylthio)phenyl]-3-(4-chloro -3-trifluoromethylphenyl)thiourea 2-(4-Aminophenylthio)naphthalene (4.2 mmoles, 1.06 g) and 4-chloro-3-trifluoromethylphenylisothiocyanate (4.2 mmoles, 0.93 g) were reacted according to procedure A to yield of the title compound 0.7 g, 34%. Mass Spec (FD) 489. Calculated for $C_{24}H_{16}ClF_3N_2S_2$: C, ; H, N, . Found: C, ; H, ; N, .

The necessary amine starting material was prepared as follows:

a) 2-Bromonaphthalene (0.08 moles, 16.6 g), 4-nitrothiophenol (0.08 moles, 12,4 g), potassium carbonate (0.1 moles, 13.4 g), copper bronze (6.0 g) and cuprous chloride (0.02 moles, 2.0 g) were heated under reflux for 4 days in 300 ml pyridine. The solution was filtered hot, concentrated, dissolved in ethyl acetate and washed thoroughly with 2N HCl and water. The solution was dried over sodium sulfate, concentrated and purified by HPLC over silica gel eluted with 5% ethyl acetate in hexane. The product was recrystallized from ethyl acetate and hexane to yield 2-(4-nitrophenylthio)naphthalene 2.6 g, 12% in the first crop. Mass spec. (FD) 281.

b) 2-(4-nitrophenylthio)naphthalene (9.2 mmoles, 2.6 g) was dissolved in 50 ml ethanol and 20 ml ethyl acetate and hydrogenated for 16 hrs at room temperature over 1.0 g 5% Pd/C. The solution was filtered through celite and concentrated to yield 2-(4-aminophenylthio)naphthalene 1.1 g, 47%.

EXAMPLE 9

1-[4-(1-Naphthylthiophenyl)-3-(4-chloro-3-trifluoromethylphenyl)thiourea 1-(4-aminophenylthio)naphthalene (20 mmoles, 5.0 g) and 4-chloro-3-trifluoromethylphenylisothiocyanate (20 mmoles, 4.7 g) were reacted according to procedure C to yield of the title compound, 2.0 g, 20%. Mass spec (FD) 488. Calculated for $C_{24}H_{16}ClF_3N_2S_2$: C, 58.95; H, 3.30, N, 5.73 Found: C, 59.17; H, 3.51; N, 5.91.

The necessary amine starting material was prepared as follows:

a) 1-Bromonaphthalene (0.15 mole, 31.0 g), 4-nitrothiophenol(0.11 mole, 17.0 g), potassium carbonate (0.15 moles, 20.7 g), copper bronze (0.3 moles, 18.9 g) and cuprous chloride (0.06 moles, 6.0 g) were refluxed in 500 ml pyridine for 3 days. The reaction was filtered while hot, and then concentrated. Ethyl acetate was added and the solution washed with water and 5N HCl, dried over sodium sulfate and concentrated. The product was purified twice by HPLC over silica gel eluted with 20% ethyl acetate/hexane followed by 5% ethyl acetate/hexane to yield 1-(4-nitrophenylthio)naphthalene 11.0 g, 26%. Mass Spec (FD) 282. Calculated for $C_{16}H_{11}NO_2S$: C, 68.31H, 3.94, N, 4.98. Found: C, 68.52; H, 4.00; N, 4.77.

b) 1-(4-Nitrophenylthio)naphthalene (39.0 mmoles, 11.0 g) was dissolved in 200 ml ethyl acetate and hydrogenated over 8 g of 5% Pd/C at 40 psi for 1 hr at room temperature. The solution was filtered through celite and the solvent removed to yield 1-(4-aminophenylthio)naphthalene 9.0 g, 92%. Mass spec (FD) 251. Calculated for $C_{15}H_{17}NS$: C, 76.46; H, 5.21, N, 5.57 Found: C, 76.71; H, 5.39; N, 5.47.

EXAMPLE 10

1-[4-(2-Benzimidazolylthio)phenyl]-3-(4-chloro-3-trifluoromethylphenyl)thiourea 2-(4-Nitrophenylthio)benzimidazole (5.0 mmoles, 1.37 g) was reduced in ethyl acetate over 1.37 g 5% Pd/C, filtered and condensed and then reacted with 4-chloro-3-trifluoromethylphenylisothiocyanate (5.0 mmoles, 1.0 g) according to procedure C to yield the title compound 0.12 g, 5% product. Mass Spec (FD) 479. Calculated for $C_{21}H_{14}ClF_3N_4S_2$: C, 52.66; H, 2.95; N, 11.70. Found: C, 52.85; H, 3.18; N, 10.47.

The necessary starting material was prepared as follows:

2-Chlorobenzimidazole (0.033 moles, 5.0 g), 4-nitrothiophenol (0.033 moles, 4.14 g), and DBU (0.033 moles, 5.0 g) in 200 ml ethanol were heated at 55° C. for 3 hr. The reaction was concentrated, ethyl acetate added, washed with water, dried over sodium sulfate and the solvent removed. The solid was slurred in hexane to yield 2-(4-nitrophenylthio)benzimidazole 1.37 g, 15%. Mass Spec (FD) 271. Calculated for $C_{13}H_8N_3O_2S$: C, 57.55; H, 3.34; N, 15.49. Found: C, 57.50; H, 5.54; N, 15.23.

EXAMPLE 11

1-[4-(2-Benzoxazolylthio)phenyl]-3-(4-chloro-3-trifluoromethylphenyl)thiourea 2-(4-Aminophenylthio)benzoxazole (10.0 mmoles, 2.6 g) and 4-chloro-3-trifluoromethylphenylisothiocyanate (10.0 mmoles, 2.4 g) were reacted according to procedure A to yield of the title compound 1.6 g, 33%. Mass Spec (FD) 479. Calculated for $C_{21}H_{13}ClF_3N_3OS_2$: C, 52.56; H, 2.73; N, 8.75. Found: C, 52.47; H, 2.70; N, 8.48.

The necessary amine starting material was prepared as follows:

2-Chlorobenzoxazole (0.065 moles, 10.0 g), 4-aminothiophenol (0.065 moles, 8.1 g) and potassium carbonate (0.065 moles, 9.0 g) were stirred for 3 days at room temperature in 250 ml ethanol, filtered, and concentrated. Ethyl acetate was added and the solution washed with water, dried over sodium sulfate and concentrated. The product was purified by HPLC over silica gel eluted with 50% ethyl acetate in hexane to yield 2-(4-aminophenylthio) benzoxazole 12.5 g, 79%. Mass spec (FD) 243. Calculated for $C_{11}H_{10}N_2OS$: C, 64.44; H, 4.16; N, 11.56. Found: C, 64.53; H, 4.22; N, 11.58.

EXAMPLE 12

1-[4-(2-Benzothiazolylthio)phenyl]-3-(4-chloro-3-trifluoromethylphenyl)thiourea 2-(4-Aminophenylthio)benzothiazole (10.0 mmoles, 2.6 g) and 4-chloro-3-trifluoromethylphenylisothiocyanate 10.0 mmoles, 2.4 g) were reacted according to procedure C to yield of the title compound, 1.5 g, 30%. Mass Spec (FD) 495. Calculated for $C_{21}H_{13}ClF_3N_3S_3$: C, 50.85H, 2.64N, 8.47. Found: C, 51.02; H, 2.71; N, 8.31.

The necessary amine starting material was prepared as follows:

2-Chlorobenzothiazole (0.06 moles, 10.1 g), 4-aminothiophenol (0.06 moles, 7.5 g) and potassium carbonate (0.06 moles, 8.3 g) were stirred for 3 days at room temperature in 250 ml ethanol, filtered, and concentrated. Ethyl acetate was added and the solution washed with water, dried over sodium sulfate and concentrated. The product was purified by HPLC over silica gel eluted with 40–60% ethyl acetate in hexane to yield 2-(4-aminophenylthio) benzothiazole 13.7 g, 88%. Mass spec (FD) 258. Calculated for $C_{11}H_{10}N_2S_2$: C, 60.44; H, 3.90; N, 10.84. Found: C, 60.63; H, 3.98; N, 11.01.

EXAMPLE 13

1-[4-(5-Chloro-2-benzothiazolylthio)phenyl]-3-(4-chloro-3-trifluoromethylphenyl)thiourea 2-(4-aminophenylthio)-5-chlorobenzothiazole (5.5 mmoles, 1.6 g) and 4-chloro-3-trifluoromethylphenylisothiocyanate (5.5 mmoles, 1.3 g) were reacted according to procedure C to yield the title compound 0.7 g, 24%. Mass Spec (FD) 529. Calculated for $C_{21}H_{12}Cl_2F_3S_3$: C, 47.55; H, 2.28; N, 7.92. Found: C, 47.55; H, 3.32; N, 7.87.

The necessary amine starting material was prepared as follows:

2,5-Dichlorobenzothiazole (0.049 moles, 10.0 g), 4-aminothiophenol (0.049 moles, 6.1 g) and DMAP (0.049 moles, 6.0 g) were stirred for 3 days at room temperature in 250 ml ethanol, filtered, and concentrated. Ethyl acetate was added and the solution washed with water, dried over sodium sulfate and concentrated. The product was purified by HPLC over silica gel eluted with 25% ethyl acetate in hexane to yield 2-(4-aminophenylthio)-5-chlorobenzothiazole 3.2 g, 22%. Mass spec (FD) 292. Calculated for $C_{13}H_9ClN_2S_2$: C, 53.33; H, 3.10; N, 9.57. Found: C, 53.03; H, 3.30; N, 9.70.

EXAMPLE 14

1-[4-(2-Quinolylsulfinyl)phenyl]-3-(4-chloro -3-trifluoromethylphenyl)thiourea 2-(4-aminophenylsulfinyl)quinoline (4.8 mmoles, 1.3 g) and 4-chloro-3-trifluoromethylphenylisocyanate (4.8 mmoles, 1.15 g) were reacted according to procedure C to yield the title compound 0.4 g, 16%. Mass Spec (FD) 505. Calculated for $C_{23}H_{15}ClF_3OS_2$: C, 58.29; H, 3.19; N, 8.87. Found: C, 58.59; H, 3.60; N, 8.27.

The necessary starting material was prepared as follows:

a) 2-(4-Nitrophenylthio)quinoline (8.8 mmoles, 2.48 g) and m-chloroperbenzoic acid (8.8 mmoles, 3.37 g) were dissolved in 100 ml methylene chloride and stirred at room temperature for 18 hr. The solution was washed with water, dried over sodium sulfate, and concentrated. The product was purified by HPLC over silica gel eluted with 40% ethyl acetate/hexane to yield 4-nitrophenyl-2-quinolylsulfone 1.5 g, 54% and 4-nitrophenyl-2-quinolylsulfoxide 0.82 g, 31%. Sulfone: Mass spec (FD) 314. Calculated for $C_{15}H_{10}N_2O_4S$: C, 57.32; H, 3.21; N, 8.91. Found: C, 57.37; H, 3.18; N, 8.72. Sulfoxide: Mass spec (FD) 266. Calculated for $C_{15}H_{10}N_2O_3S$: C, 60.39; H, 3.38; N, 9.39. Found: C, 60.64; H, 3.18; N, 8.72.

b) 4-Nitrophenyl-2-quinolylsulfone (9.0 mmoles, 2.7 g) was dissolved in 200 ml ethanol and 75 ml DMF and was then hydrogenated over 2.2 g 5% Pd/C at room temperature for 3 hr. The reaction mixture was then filtered through celite and condensed to afford 2-(4-aminophenylsulfinyl)quinoline

EXAMPLE 15

1-[4-(2-Quinolylsulfonyl)phenyl]-3-(4-chloro-3-trifluoromethylphenyl)thiourea 2-(4-Aminophenylsulfonyl)quinoline (5.3 mmoles) and 4-chloro-3-trifluoromethylphenylisocyanate (5.8 mmoles, 1.38 g) were reacted according to procedure A to yield the title compound, 0.6 g, 2%. Mass Spec (FD) 521. Calculated for $C_{23}H_{15}ClF_3N_3O_2S_2$: C, 52.93; H, 2.90; N, 8.05. Found: C, 53.21; H, 3.09; N, 8.25.

The necessary amine starting material was prepared as follows:

4-Nitrophenyl-2-quinolylsulfoxide (5.3 mmoles, 1.5 g) prepared as described in Example (14, step a), was dissolved in ethanol/ethyl acetate and hydrogenated over 1 g 5% Pd/C at room temperature for 3 hr. The reaction mixture was then filtered through celite and condensed to afford 2-(4-aminophenylsulfonyl)quinoline Mass spec (FD) 284. Calculated for $C_{15}H_{12}N_2O_2S$: C, 63.36; H, 4.25; N, 9.85. Found: C, 62.16; H, 4.25; N, 9.25.

EXAMPLE 16

1-[4-(2-quinolylamino)phenyl]-3-(4-chloro-3-trifluoromethylphenyl)thiourea 2-(4-aminophenylamino)quinoline (5.0 mmoles, 1.15 g) and 4-chloro-3-trifluoromethylphenylisothiocyanate (5.0 mmoles, 1.20 g) were reacted according to procedure C of to yield the title compound 1.60 g, 68%. Mass Spec (FD) 473. Calculated for $C_{23}H_{16}ClF_3N_4S$: C, ; H, ; N, . Found: C, ; H, ; N, .

EXAMPLE 17

1-[4-(2-Quinolyloxy)phenyl]-3-(4-chloro-3-trifluoromethylphenyl)thiourea 2-(4-Aminophenoxy)quinoline (2.4 mmoles, 0.56 g) and 4-chloro-3-trifluoromethylphenylisothiocyanate (2.4 mmoles, 0.57 g) were reacted according to procedure C to yield the title compound, 0.8 g. 70%. Mass Spec (FD) 473. Calculated for $C_{23}H_{15}ClF_3N_3OS$: C, 58.29; H, 3.19; N, 8.87. Found: C, 58.47; H, 3.48; N, 8.85.

The necessary amine starting material was prepared as follows:

a) 4-Nitrophenol(41 mmoles, 5.1 g) was dissolved in DMF (500 ml) and treated with sodium hydride (41 mmoles previously washed with hexane). After stirring at room temperature for 1 hr, 2-chloroquinoline (40 mmoles, 6.5 g) was added dropwise and stirred for 16 hr at room temperature followed by refluxing for 6 hr. Water was added to the cooled solution and the product was extracted with ethyl acetate. The ethyl acetate solution was washed with water, and 5N NaOH, dried over sodium sulfate and concentrated. The product was purified by HPLC over silica gel eluted with ethyl acetate/hexane to yield 2-(4-nitrophenoxy) quinoline. 3.1 mmoles, 8%. Mass Spec (FD) 266. Calcd for $C_{15}H_{10}N_2O_3$: C 67.45; H, 3.84; N, 10.40. Found: C, 65.84; H, 3.88; N, 8.47.

b) 2-(4-Nitrophenoxy)quinoline(3 mmoles, 0.82 g) was dissolved in 100 ml ethyl acetate and hydrogenated over 2.0 g 5% Pd/C at room temperature for 1 hr. The solution was filtered through cellulose and concentrated to yield 2-(4-aminophenoxy)quinoline 0.58, 82%. Mass Spec (FD) 236. Calculated for $C_{15}H_{12}N_2O$: C, 76.25; H, 5.12, N, 11.86. Found: C, 75.97; H, 5.37; N, 11.83.

EXAMPLE 18

1-[4-(2-Quinolylthio)phenyl]-3-(4-chloro-3-trifluoromethylphenyl)urea 2-(4-Aminophenylthio)quinoline (3.9 mmoles, 1.0 g) and 4-chloro-3-trifluoromethylphenylisocyanate (3.9 mmoles, 0.85 g) were reacted according to procedure A to yield the title compound, 0.8 g, 43%. Mass Spec (FD) 463. Calculated for $C_{23}H_{15}ClF_3N_3OS$: C, 58.29; H, 3.19; N, 8.87. Found: C, 58.56; H, 3.43; N. 9.02. M Pt 194°–195° C.

EXAMPLE 19

1-[4-(2-Quinolylthio)phenyl]-3-(3,4-dichlorophenyl)thiourea 2-(4-Aminophenylthio)quinoline 11.9 mmoles, 3.0 g) and 3,4-dichlorophenylisothiocyanate 11.9 mmoles, 2.42 g) were reacted according to procedure B to yield the title compound, 360 mg, 6.6%. Mass Spec (FD) 455. Calculated for $C_{22}H_{15}Cl_2N_3S_2$: C, 57.90 H. 3.31; N, 9.21. Found: C, 57.86; H, 3.53; N, 9.07. m.p. 125°–126°.

The necessary amine starting material was prepared as follows:

a) 2-Chloroquinoline (0.12 moles, 20.0 g), 4-nitrothiophenol (0.13 mmoles, 20.8 g), and potassium carbonate (0.13 moles, 18.5 g) were dissolved in 800 ml ethanol and stirred at room temperature for 1.5 hr. The mixture was filtered and the solid washed with ethanol. The solid was dissolved with ethyl acetate, washed with water, dried over sodium sulfate and concentrated to yield 2-(4-nitrophenylthio)quinoline 26.0 g, 77%. Mass Spec (FD) 282. Calculated for $C_{15}H_{10}N_2O_2S$: C, 63.82, H 3.57; N, 9.92. Found: C, 63.55, H 3.59; N, 9.71.

b) 2-(4-Nitrophenylthio)quinoline (0.42 moles, 12.0 g) was hydrogenated in 300 ml DMF over 5.0 g Pd/C for 3 hr at room temperature. The solution was filtered through celite and concentrated. The product was triturated with ether and hexane to yield 2-(4-aminophenylthio)quinoline 10.0 g, 93%.

EXAMPLE 20

1-[4-(6-phenyl-3-pyridazylthio)phenyl]-3-(4-chloro-3-trifluoromethylphenyl)thiourea 3-(4-aminophenylthio)-6-phenylpyridazine (7.0 mmoles, 2.0 g) and 4-chloro-3-trifluoromethylphenylisothiocyanate (7.0 mmoles, 1.66 g) were reacted according to procedure C to yield of the title compound 2.5 g, 69%. Mass Spec (FD) 516. Calculated for $C_{24}H_{16}ClF_3N_4O_2S_2$: C, 55.76; H, 3.12; N, 10.84. Found: C, 55.98 H, 3.19; N, 10.78.

The necessary amine starting material was prepared as follows:

3-Chloro-6-phenylpyridazine (0.026 moles, 5.0 g), 4-aminothiophenol (0.026 moles, 3.3 g) and potassium carbonate (0.026 moles, 3.6 g) were stirred in 250 ml ethanol for 3 days. The reaction was filtered, concentrated, ethyl acetate added, washed with water and dried over sodium sulfate. The solution was concentrated and the product purified by HPLC over silica gel eluted with 50% ethyl acetate/hexane to yield 3-(4-aminophenylthio)-6-phenylpyridazine 6.0 g, 83%. Mass Spec (FD) 279. Calculated for $C_{16}H_{13}N_3S$: C, 68.79; H, 4.69; N, 15.04. Found: C, 68.87; H, 4.43N, 15.31.

EXAMPLE 21

1-[4-(2-pyridylthio)phenyl]-3-(4-chloro-3-trifluoromethylphenyl)thiourea.

2-(4-Aminophenylthio)pyridine (6.0 mmoles, 1.2 g) and 4-chloro-3-trifluoromethylphenylisothiocyanate (6.0 mmoles, 1.4 g) were reacted according to procedure C to yield the title compound, 1.9 g, 72%. Mass spec (FD) 439. Calculated for $C_{19}H_{13}ClF_3N_3S_2$: C, 51.88; H, 2.98, N, 9.55 Found: C, 51.99; H, 3.15; N, 9.63.

The necessary amine starting material was prepared as follows:

4-Aminothiophenol (0.065 moles, 8.1 g) in 275 ml DMF was stirred at room temperature for 1 hr with sodium hydride (0.065 moles previously washed with hexane). 2-Chloropyridine (0.06 moles, 6.8 g) was added and the reaction mixture was stirred for 6 hr. An additional 5.2 g of 4-aminothiophenol was added and the reaction stirred at room temperature for 16 hr. Water was added and the product extracted with ethyl acetate. The solution was washed thoroughly with water, dried over sodium sulfate and concentrated. The product was purified by HPLC over silica gel eluted with 30% ethyl acetate/hexane to yield 2-(4-aminophenylthio)pyridine 1.2 g, 10%. Mass spec (FD) 202. Calculated for $C_{11}H_{10}N_2S$: C, 65.32; H, 4.98, N, 13.85 Found: C, 65.23; H, 5.09; N, 13.63.

EXAMPLE 22

1-[4-(5-Nitroquinol-6-ylthio)phenyl-3-(4-chloro-3-trifluoromethylphenyl)thiourea.

5-nitro-6-(4-aminophenylthio)quinoline 1.7 mmoles, 0.40 g) and 4-chloro-3-trifluoromethylphenylisothiocyanate 1.7 mmoles, 0.47 g) were reacted according to procedure C to yield the title compound, 0.78 g, 86% product. Mass spec (FD) 534. Calculated for $C_{23}H_{14}ClF_3N_4O_2S_2$: C, 51.64; H, 2.64, N, 10.47 Found: C, 51.84; H, 2.73; N, 10.43.

EXAMPLE 23

1-[2-(5-bromo-1,3,4-thiadiazolyl]-3-(2-naphthyl)urea

A solution of 2-naphthanoic acid(5.0 mmole, 0.86 g) and triethylamine (6.0 mmole, 0.61 g) in tetrahydrofuran(25 ml) cooled to 0° was treated with diphenylphosphoryl azide (5.5 mole, 1.51 g). The reaction was stirred at 22° C. for 30 minutes, the reaction was treated with 2-amino-5-bromo-1,3,4-thiadiazole (5.0 mmole, 0.90 g). The reaction mixture was then stirred at 22° C. for 30 minutes, then heated to 60° C. After stirring at 60° C. for approximately 22 hours, the reaction mixture was cooled to ambient temperature, the insolubles were collected by filtration and washed with tetrahydrofuran (2 ml). The filtrate was concentrated in vacuo to an oil. The oil was treated with methylene chloride (25 ml), washed with 0.1N sodium hydroxide (2×10 ml) hydrochloric acid (2×10 ml) and brine (10 ml). The organic phase was then subjected to silica gel column chromatography eluting with a 0 to 35% methanol:toluene. Fractions containing the desired material were combined and concentrated in vacuo to afford a solid. This material was treated with hot tetrahydrofuran (20 ml), filtered through Celite 521, reduced in volume and treated with hexane (6 ml). The insolubles were collected by filtration and washed with 3:1 hexane:tetrahydrofuran (9 ml). The filtrate was subjected to radial band chromatography to afford the title compound.

Analysis calculated for $C_{13}H_9BrN_4OS$: %C, 44.71; %H, 2.60; %N, 16.04. Found: %C, 44.97; %H, 2.77; %N, 15.83.

Field Desorption Mass Spectrum: M−1=348.

EXAMPLE 24

1-[2-(5-bromo-1,3,4-thiadiazolyl]-3-(1-naphthyl)urea

Following a method similar to that described in Example 23, but using 1-naphthylisocyanate instead of 2-amino-5-chloro-1,3,4-thiadiazole, the title compound was prepared.

Analysis calculated for $C_{13}H_9BrN_4OS$: %C, 44.71; %H, 2.60; %N, 16.04. Found: %C, 45.00; %H, 2.59; %N, 16.14.

Field Desorption Mass Spectrum: M−1=348.

We claim:

1. A method of inhibiting the production of Aβ peptide in a biological system, which comprises administering an effective amount of a compound of general formula

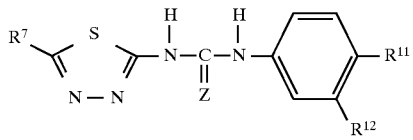

Ia in which
- Z is O or S;
- $R^{11}$ is a halogen atom;
- $R^{12}$ is a halogen atom or a trifluoromethyl group; and
- $R^7$ is hydrogen, (1–8C)alkyl, (1–8C)haloalkyl, (1–8C)alkylthio, (1–8C)alkoxy or halogen;

or a pharmaceutically acceptable salt thereof.

2. A method as claimed in claim 1, in which Z is O, $R^{11}$ is a fluorine or chlorine atom, and $R^{12}$ is a chlorine atoms or a trifluoromethyl group.

3. A method as claimed in claim 2 in which $R^7$ is hydrogen, methyl, t-butyl, trifluoromethyl, 2chloro-2-methylpropyl, hexylthio, bromo or chloro.

4. A method as claimed in claim 1, in which the compound of formula 5 is selected from 1-1,3,4-thiadiazol-2-yl)-3-(3,4-dichlorophenyl)urea;

1-(5-chloro-1,3,4-thiadiazol-2-yl)-3-(3,4-dichlorophenyl)urea;

1-(5-trifluoromethyl-1,3,4-thiadiazol-2-yl)-3-(3,4-dichlorophenyl)urea;

1-(5-t-butyl-1,3,4-thiadiazol-2-yl)-3-(3,4-dichlorophenyl)urea;

1-[5-(2-chloro-1,1-dimethylethyl)-1,3,4-thiadiazol-2-yl]-3-(3,4-dichlorophenyl)urea;

1-(5-hexylthio-1,3,4-thiadiazol-2-yl)-3-(3,4-dichlorophenyl)urea;

1-(5-bromo-1,3,4-thiadiazol-2-yl)-3-(3,4-dichlorophenyl)urea;

1-(5-methyl-1,3,4-thiadiazolyl)-3-(4-fluoro-3-chlorophenyl)urea; and 1-(5-methyl-1,3,4-thiadiazolyl)-3-(3,4-dichlorophenyl)urea or a pharmaceutically acceptable salt thereof.

5. A method of inhibiting the accumulation of Aβ peptide in senile plaques in a warm-blooded mammal, which comprises administering an effective amount of a compound of general formula.

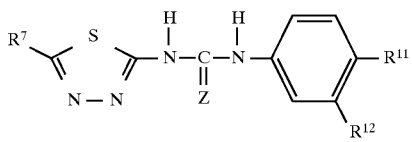

Ia in which
- Z is O or S;
- $R^{11}$ is a halogen atom;
- $R^{12}$ is a halogen atom or a trifluoromethyl group; and
- $R^7$ is hydrogen, (1–8C)alkyl, (1–8C)haloalkyl, (1–8C)alkylthio, (1–8C)alkoxy or halogen;

or a pharmaceutically acceptable salt thereof.

6. A method of protecting a warm-blooded mammal from the progression of Alzheimer's disease by inhibiting the formation of Aβ peptide, which comprises administering an effective amount of a compound of general formula.

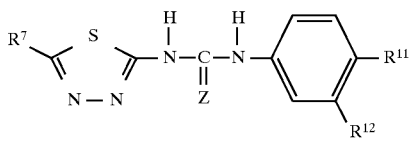

Ia in which
- Z is O or S;
- $R^{11}$ is a halogen atom;
- $R^{12}$ is a halogen atom or a trifluoromethyl group; and
- $R^7$ is hydrogen, (1–8C)alkyl, (1–8C)haloalkyl, (1–8C)alkylthio, (1–8C)alkoxy or halogen;

or a pharmaceutically acceptable salt thereof.

* * * * *